US008530269B2

(12) United States Patent
Chua et al.

(10) Patent No.: US 8,530,269 B2
(45) Date of Patent: Sep. 10, 2013

(54) MANUFACTURE OF A POLYMER DEVICE

(75) Inventors: Lay-Lay Chua, Hillington Green (SG);
Peter Kian-Hoon Ho, Hillington Green (SG); Richard H. Friend, Cambridge (GB)

(73) Assignee: Cambridge Enterprise Ltd, Cambridge (GB)

( * ) Notice: Subject to any disclaimer, the term of this patent is extended or adjusted under 35 U.S.C. 154(b) by 472 days.

(21) Appl. No.: 10/556,841

(22) PCT Filed: May 12, 2004

(86) PCT No.: PCT/GB2004/002078
§ 371 (c)(1),
(2), (4) Date: Sep. 27, 2006

(87) PCT Pub. No.: WO2004/100282
PCT Pub. Date: Nov. 18, 2004

(65) Prior Publication Data
US 2007/0172978 A1 Jul. 26, 2007

(30) Foreign Application Priority Data

| May 12, 2003 | (GB) | ................................. | 0310858.6 |
| Jul. 4, 2003 | (GB) | ................................. | 0315731.0 |
| Apr. 16, 2004 | (GB) | ................................. | 0408539.5 |

(51) Int. Cl.
*H01L 51/40* (2006.01)
(52) U.S. Cl.
USPC ...... 438/99; 438/758; 438/780; 257/E51.001; 257/E51.027

(58) Field of Classification Search
USPC ........... 438/99–199, 758–780; 257/E51.001, 257/E51.027
See application file for complete search history.

(56) References Cited

U.S. PATENT DOCUMENTS

| 5,039,208 A | * | 8/1991 | Ohnishi et al. | ................ 349/191 |
| 5,523,555 A | | 6/1996 | Friend et al. | ............. 250/214 R |

(Continued)

FOREIGN PATENT DOCUMENTS

| EP | 293 911 A2 | 12/1988 |
| EP | 880 303 A1 | 11/1998 |

(Continued)

OTHER PUBLICATIONS

"Azide-Phenolic Resin Photoresists for Deep UV Lithography", Iwayanagi et al., IEEE Transactions on Electron Devices, vol. ED-28, No. 11, Nov. 1981, pp. 1306-1310.

(Continued)

*Primary Examiner* — Charles Garber
*Assistant Examiner* — Abdulfattah Mustapha
(74) *Attorney, Agent, or Firm* — Marshall, Gerstein & Borun LLP

(57) ABSTRACT

A method of forming a polymer device including the steps (i) of depositing on a substrate a solution containing a polymer or oligomer and a crosslinking moiety, to form a layer, and, (ii) curing the layer formed in step (i) under conditions to form an insoluble crosslinked polymer, wherein the crosslinking moiety is present in step (i) in an amount in the range of from 0.05 mol % to 5 mol % based on the total number of moles or repeat units of the polymer or oligomer and the crosslinking moiety in the solution.

24 Claims, 13 Drawing Sheets

(56) References Cited

U.S. PATENT DOCUMENTS

| | | | |
|---|---|---|---|
| 5,682,043 A * | 10/1997 | Pei et al. | 257/40 |
| 6,096,018 A * | 8/2000 | Luzio et al. | 604/500 |
| 6,107,452 A | 8/2000 | Miller et al. | 528/422 |
| 6,603,139 B1 * | 8/2003 | Tessler et al. | 257/40 |
| 2002/0106529 A1 * | 8/2002 | Okunaka et al. | 428/690 |
| 2003/0048975 A1 * | 3/2003 | Lackritz et al. | 385/14 |
| 2005/0146263 A1 * | 7/2005 | Kelly et al. | 313/504 |
| 2005/0280020 A1 * | 12/2005 | Heeger et al. | 257/103 |
| 2006/0088787 A1 * | 4/2006 | Gonsalves et al. | 430/281.1 |

FOREIGN PATENT DOCUMENTS

| | | |
|---|---|---|
| JP | 10-511718 | 11/1998 |
| JP | 11-510535 | 9/1999 |
| JP | 2002-506481 | 2/2002 |
| JP | 2002-170667 | 6/2002 |
| WO | WO 90/13148 | 11/1990 |
| WO | WO 94/03030 | 2/1994 |
| WO | WO 96/16449 | 5/1996 |
| WO | WO 96/20253 | 7/1996 |
| WO | WO 97/05184 | 2/1997 |
| WO | WO 99/54385 | 10/1999 |
| WO | WO 03/095586 A1 | 11/2003 |

OTHER PUBLICATIONS

"Bis(perfluorophenyl) Azides: Efficient Cross-Linking Agents for Deep-UV and Electron Beam Lithography", Cai et al., Chem. Mater., vol. 2, No. 6, 1990, 3 pages.

"Development of Highly Efficient Deep-UV and Electron Beam Mediated Cross-Linkers: Synthesis and Photolysis of Bis(perfluorophenyl) Azides", Cai et al., Chem. Mater. 6, 1994, pp. 1822-1829.

"Progress with Light-Emitting Polymers", Bernius et al., Adv. Mater. 12, No. 23, Dec. 1, 2000, pp. 1737-1750.

"Synthesis and Properties of Novel Triphenylamine Polymers Containing Ethynyl and Aromatic Moieties", Kim et al., Synthetic Metals 122, 2001, pp. 363-368.

"I-Line Lithography of Poly-(3,4-ethylenedioxythiophene) Electrodes and Application in All-Polymer Integrated Circuits", Touwslager et al., Applied Physics Letters, vol. 81, No. 24, Dec. 9, 2002, pp. 4556-4558.

"Multi-Colour Organic Light-Emitting Displays by Solution Processing", Muller et al., Nature, vol. 421, Feb. 20, 2003, pp. 829-833.

International Search Report in PCT/GB2004/002078 dated Nov. 22, 2004.

Written Opinion in PCT/GB2004/002078, Nov. 22, 2004.

* cited by examiner

MANUFACTURE OF A POLYMER DEVICE

The present invention is concerned with a method for making a polymer device. In particular, the present invention is concerned with a method of depositing a polymer layer in a method for making a polymer device. The present invention also is concerned with devices, such as electronic and optoelectronic devices, preparable by the present method.

Polymer devices include polymer light-emitting diodes (LEDs), photodetectors, photovoltaics (PVs) and field-effect transistors (FETs). Such devices typically comprise one or more semiconductive polymer layers located between electrodes. Semiconductive polymers are characterized by partial or substantial pi-conjugation in the backbone or side chains.

Semiconductive polymers are now frequently used in a number of optical devices such as in polymeric light emitting diodes ("PLEDs") as disclosed in WO 90/13148; field effect transistors ("FETs"); photovoltaic devices as disclosed in WO 96/16449; and photodetectors as disclosed in U.S. Pat. No. 5,523,555.

A typical PLED comprises a substrate, on which is supported an anode, a cathode, and an organic electroluminescent layer located between the anode and cathode and comprising at least one polymeric electroluminescent material. In operation, holes are injected into the device through the anode and electrons are injected into the device through the cathode. The holes and electrons combine in the organic electroluminescent layer to form an exciton, which then undergoes radiative decay to give light. Other layers may be present in the PLED. For example a layer of organic hole injection material such as poly(ethylene dioxy thiophene)/polystyrene sulfonate (PEDT/PSS) may be provided between the anode and the organic electroluminescent layer to assist injection of holes from the anode to the organic electroluminescent layer.

Transistors, and specifically field-effect transistors (FETs), are three-terminal devices which comprise a source contact, a drain contact, and a gate contact. A semiconductive layer (channel) bridges the source and drain contacts, and is itself spaced from the gate contact by an insulating layer called the gate dielectric. In polymer transistors, the semiconductive layer is fabricated from a semiconductive polymer, typically a π-conjugated organic polymer. This layer may be deposited in the device by a precursor route or directly by solution-processing.

A voltage is applied across the source contact and the drain contact. Further, in a field effect transistor, a voltage is applied to the gate contact. This voltage creates a field which causes accumulation or depletion of charge carriers in the semiconductive layer lying directly under the gate dielectric. This in turn controls the current flowing from the source to the drain contact for a given source-drain voltage.

In the case of a phototransistor, light of the appropriate wavelength is allowed to fall on the channel. The photons can generate hole-electron pairs which split and contribute to current flowing between the source and drain, thereby modulating the source-drain conductivity.

As described in WO 96/16449, a typical photovoltaic device comprises a photoresponsive zone having first and second major surfaces and first and second electrodes provided on respective ones of the first and second major surfaces of the photoresponsive zone. The photoresponsive zone comprises a first semiconductive polymer optionally blended with a second semiconductive polymer that is phase-separated from the first semiconductive polymer. Under short-circuit conditions, an internal electric field exists within the photoresponsive zone. The orientation of the internal electric field is such that electrons migrate to and are collected at the contact with the lowest work function, generally an aluminium, magnesium or calcium electrode while holes move towards the electrode with the higher work function, such as an indium tin oxide electrode. Thus, a photocurrent can be detected and may be used, for example, to provide electrical power as in the case of a solar cell, for example, or to enable detection of part of a light pattern such as an image for use in an image sensor.

As discussed in U.S. Pat. No. 5,523,555 a typical photodetector device includes a photoresponsive layer arranged between first and second electrode layers having different work functions. The photoresponsive layer comprises a semiconductive polymer or blend of polymers. There may be a plurality of photoresponsive layers. A bias circuitry is connected to apply a bias voltage between the first and second electrode layers. A sensing circuitry is connected to detect a photocurrent flowing between the first and second electrode layers across the polymer layer as a result of radiation incident on the polymer layer while the bias voltage is applied. The bias voltage is selected in relation to the distance between the electrodes.

Semiconductive polymers can exhibit a wide range of photophysical properties (such as the π-π*bandgap and photoluminescent yield); optical properties (such as refractive index and its dispersion); electronic properties (such as hole- and electron-transport energy levels, and hole- and electron-mobilities); and processing properties (such as solvent solubility, phase transition temperature, crystallinity and phase-transition temperatures). These properties are largely controlled by the chemical structure of the polymer. In this regard, these properties largely may be controlled within a range by appropriate selection of the backbone units and side chains of the polymer.

The polymer or polymers in the afore-mentioned polymer devices are preferably soluble in common organic solvents to facilitate their deposition during device manufacture. One of the key advantages of this solubility is that a polymer layer can be fabricated by solution processing, for example by spin-casting, ink-jet printing, screen-printing, dip-coating etc. Examples of such polymers are disclosed in, for example, Adv. Mater. 2000 12(23) 1737-1750 and include polymers with at least partially conjugated backbones formed from aromatic or heteroaromatic units such as fluorenes, indenofluorenes, phenylenes, arylene vinylenes, thiophenes, azoles, quinoxalines, benzothiadiazoles, oxadiazoles, thiophenes, and arylamines with solubilising groups, and polymers with non-conjugated backbones such as poly(vinyl carbazole). Polyarylenes such as polyfluorenes have good film forming properties and may be readily formed by Suzuki or Yamamoto polymerisation which enables a high degree of control over the regioregularity of the resultant polymer.

In certain devices it can be desirable to cast multiple layers, i.e., laminates, of different polymers on a single substrate surface. For example, this could be to achieve optimisation of separate functions, for example electron or hole charge transport, luminescence control, photon-confinement, exciton-confinement, photo-induced charge generation, and charge blocking or storage.

In this regard, it can be useful to be able to fabricate multilayers of such polymers to control the electrical and optical properties, for example, across the polymer stack. This can be useful for optimum device performance. Optimum device performance can be achieved, for example, by careful design of the electron and hole transport level offset, of the optical refractive index mismatch, and of the energy gap mismatch across the interface. Such heterostructures can, for example, facilitate the injection of one carrier but block the extraction of the opposite carrier and/or prevent exciton diffusion to the quenching interface. Thereby, such heterostructures can provide useful carrier and photon confinement effects.

It also can be useful to be able to fabricate multilayers in order to provide a protective layer in the device structure. In this regard, taking one example, it is believed that PEDT/PSS may have a deleterious effect on the electroluminescent layer of PLEDs. Without wishing to be bound by theory, it is thought that this may be due to electrochemical reactions between the PEDT:PSS layer and the electroluminescent layer (i.e. the layer in which holes and electrons combine to form an exciton). It is thought that this results in quenching of luminescence and progressive increase in required drive voltage. Accordingly, it may be desirable to provide a protective layer between PEDT:PSS and the electroluminescent layer.

However, preparation of polymer laminates is not generally trivial. In particular, the solubility of initially cast or deposited layers in the solvents used for succeeding layers can be problematic. This is because solution deposition of the subsequent polymer layer can dissolve and destroy the integrity of the previous layer.

One option for overcoming this problem is to work with precursor polymer systems. Precursor systems of PPV (polyphenylene vinylene) and PTV (polythienylene vinylene) are known in this art.

Layers of semiconducting polymers may be formed by depositing a soluble polymeric precursor which is then chemically converted to an insoluble, electroluminescent form. For example, WO 94/03030 discloses a method wherein insoluble, electroluminescent poly(phenylene vinylene) is formed from a soluble precursor and further layers are then deposited from solution onto this insoluble layer.

However, it is clearly undesirable to restrict the polymer in a polymer device to that class of polymers that may be formed from insoluble precursor polymers. Furthermore, the chemical conversion process required for precursor polymers involves extreme processing conditions and reactive by-products that may harm the performance of the prior layers in the finished device.

A further option for overcoming this problem is to use polymers that differ widely in their solubility behaviour. For example, the use of a polymer that is soluble in a hydrocarbon solvent in conjunction with a polymer that is soluble in water or in an acetate solvent can allow the preparation of a limited bilayer or trilayer stack. An important example in this respect is the deposition of a conjugated polymer from an aromatic hydrocarbon solvent over a first-formed conductive PEDT: PSS film that is not soluble in the aromatic hydrocarbon solvent. Again, this severely restricts the classes of polymers that can be used in a multilayered stack. This is because most conjugated polymer systems are characterized by solubility in the same set of aromatic hydrocarbon solvents (such as xylenes and other substituted benzenes) and mildly polar hydrocarbon solvents (such as tetrahydrofuran, and halogenated solvents).

It will be appreciated that limitations on the polymers that are useable in the laminate mean that many concepts of device structure cannot be investigated or implemented. As such, the further development of device architecture becomes heavily impeded.

WO96/20253 generally describes a luminescent film-forming solvent processable polymer which contains crosslinking. It is stated that because the thin films resist dissolution in common solvents this enables deposition of further layers, thereby facilitating device manufacture. The use of azide groups attached to the polymer main chain are mentioned as an example of thermal crosslinking. In the general formula shown on page 7, the polythiophene copolymer contains repeat units having crosslinking moieties at a level in the range of from 5 mol % to 66 mol %.

U.S. Pat. No. 6,107,452 discloses a method of forming a multilayer device wherein fluorene containing oligomers comprising terminal vinyl groups are deposited from solution and cross-linked to form insoluble polymers onto which additional layers may be deposited. The vinyl units must be present at a mol ratio above at least 25%. This is dictated by the mechanism via which crosslinking occurs in U.S. Pat. No. 6,107,452.

Similarly, Kim et al, Synthetic Metals 122 (2001), 363-368 discloses polymers comprising triarylamine groups and ethynyl groups which may be cross-linked following deposition of the polymer. This document discloses ethynyl groups present at 100 mol % as part of the repeat unit of a polymer.

In addition to uses in forming a polymer laminate, rendering a polymer insoluble after deposition also enables negative-tone lithography. According to standard negative-tone photoresist lithography, polymer films, often polystyrene or poly(methylmethacrylate), containing a critical loading of a crosslinking system are cast onto a substrate. Selected areas are exposed through a mask pattern. The regions that are exposed become insoluble through a crosslinking reaction. The regions that are unexposed remain soluble and can be removed subsequently by washing with a developer solvent system, resulting in the transfer of the negative image of the mask onto the photoresist film.

In this regard, it is desirable to form full colour displays by patterning of red, green and blue electroluminescent materials. It is also desirable to pattern and isolate individual FETs or photodetector elements that are formed on a substrate. Known methods include patterned deposition of solution processable materials, in particular polymers, by inkjet printing as disclosed in, for example, EP 0880303 or by evaporation of evaporable materials through a shadow mask.

One method is to incorporate polymerisable moieties in the side chains of the polymer, and initiate the polymerisation (crosslinking) reaction via a radiation-sensitive initiator. An example of this method is described in Nature 421, 829-833, 2003 which discloses a method of forming a full colour display by deposition of layers of red, green and blue electroluminescent polymers bearing oxetane side groups which are cross linked via a photoacid generator after deposition by exposure to the appropriate radiation. The oxetane containing monomers are incorporated into the exemplified polymers at a level of 25 mol %. Only selected areas of each layer are exposed to UV illumination through a mask to cross-link the selected areas. Polymer in unexposed areas remains soluble and so may be washed away to leave a patterned layer. This method as disclosed, however, results in polymers with depressed electron and hole mobilities. Furthermore oxetanes are prone to self-polymerisation in the presence of trace acid catalyst in storage.

An alternative approach is to employ low molecular mass radiation-sensitive crosslinkers in the polymer-solvent formulation.

In this respect, the use of bisarylazides is disclosed in T Iwayanagi, T Kohashi, S Nonogaki, T Matsusawa, K Douta, H. Yanazawa, IEEE Transactions on Electronic Devices ED25 (1981) pp. 1306. This document discloses a photosensitive composition consisting of an aromatic azide compound and a phenolic resin as a negative deep UV resist for lithography. The azide compound is mixed with the phenolic resin in the range of 5 to 30 wt %.

Further, in S. X. Cai, D. J. Glenn, M. Kanskar, M. N. Wybourne and J. F. W. Keana, "Development of highly efficient deep-uv and electron beam mediated cross-linkers: synthesis and photolysis of bis(perfluorophenyl) azides" Chemistry of Materials, 6 (1994) pp. 1822-1829], the use of bis (perfluorophenylene azide)s for the purpose of negative resist formulation has been disclosed. In this disclosure, the bis (perfluorophenylene azide) is blended with poly(styrene) which is a conventional lithography polymer. This document does not disclose polymer devices.

Although the use of crosslinkers is thus known in the fields of negative-resist electron beam and optical lithographies, the requirements of a negative lithographic resist (NLR) formulation and that of a crosslinkable formulation for semiconductive polymers (SP) are vastly different:
(1) NLR formulations typically comprise a non-absorbing polymer matrix and a crosslinker system that is sensitive to the desired radiation. Because the polymer matrix is substantially transparent to the radiation wavelengths of interest, it does not by itself impose requirements on the spectral wavelengths at which the crosslinker system needs to be sensitised. Therefore the spectral sensitivity of the crosslinker system is essentially dictated by the radiation wavelength of choice. In contrast, SPs are characterized by strong optical absorption bands in the optical and ultraviolet wavelength ranges. Such absorption features are fundamental to the nature and usefulness of SPs in devices. Because the absorption intensities of their primary absorption bands are rather large, the corresponding absorption depth is shallow and the SP films are practically opaque at these wavelengths. For example, this 1/e absorption depth (or equivalently, the radiation penetration depth) is typically less than 50 nm at band maximum for most SPs. The crosslinking system therefore advantageously should have its spectral sensitivity matched to the limited transparency window in between the strong absorption bands for each SP. Crosslinking systems which do not satisfy this requirement may only crosslink the topmost layer of the film which therefore limits their usefulness in SPs. Furthermore, it is also advantageous to be able to use wavelengths at which the SP is substantially non-absorbing to avoid an attendant photo-induced oxidation and other reactions.
(2) NLR formulations are not used as the active layer in semiconductor devices. They are employed as sacrificial mask layers and are therefore not subject to the stringent requirements of the crosslinkable SP formulations to be used in devices. In particular, in SP formulations, the crosslinker system should not introduce significant concentrations of electron traps, hole traps or exciton traps which can degrade the performance of the device. For example, some well known photogenerated acid (PGA) chemically amplified resist systems leave PGA residues that can severely interfere with the charge-transport and luminescence properties of conjugated polymers.

The use of non-fluorinated bis(phenyl azide)s as a radiation-sensitive crosslinker to formulate a negative photoresist based on the conducting polymer PEDT:PSS has recently been disclosed in F. J. Touwslager, N. P. Willard and D. M. de Leeuw, "I-line lithography of poly(3,4-ethylenedioxythiophene) electrodes and application in all-polymer integrated circuits" Applied Physics Letters, 81 (2002) pp. 4556-4558. This describes photolithographic patterning of conductive, as distinct from semiconductive, polymer lines to form electrodes and interconnects. The PEDT:PSS is crosslinked with bis(phenyl azide) upon exposure to 365-nm I-line radiation. A principle characteristic of this method (as with the azide method of WO96/20253) is that the phenyl azides as a class of material are rather inefficient as crosslinkers, which necessitates their incorporation at a high concentration. Furthermore, there are many side-products of the crosslinking reaction, and many of these are toxic to device performance.

A similar method is described in US 2002/106529 wherein an electroluminescent material is blended with or bound to a polymeric binder. The binder polymer may be crosslinked. Some binder polymers having a photo-crosslinkable group have a repeating unit represented by general formula (9), as disclosed on page 5. Clearly, these materials have a high mol % content of photo-crosslinkable groups. Alternatively, a photo-crosslinking moiety may be mixed with the binder polymer and, in this embodiment, it is taught that this agent should mixed in an amount of from 5 to 50 parts by weight, based on 100 parts by weight of the binder polymer.

The systems disclosed in the prior art, and particularly those disclosed in the above Applied Letters Physics disclosure, US 2002/106529, WO96/20253, and U.S. Pat. No. 6,107,452, are not particularly suitable for use within devices. The disclosed crosslinking processes are based on polymerisation or on specific coupling between two crosslinking moieties. For this to occur efficiently, the crosslinker moieties must be present at very high loadings (substantially more than 5 mol %). The high loading of crosslinker moieties per se or the by-products of the reaction of the crosslinker moieties tend to interfere with efficient charge-carrier transport in the device layers. Further, the crosslinker moieties can interfere indirectly with efficient charge-carrier transport through their dilution and disordering effects. By "dilution effects" is meant the effects that arise as a consequence of the decreasing relative concentration of conjugated segments in the polymer as the loading of the crosslinked moieties in the final product increases. By "disordering effects" is meant the twisting of the backbone of the final crosslinked polymer out of the plane due to high loadings of crosslinked moieties. As a result the drive voltage of the devices will correspondingly be increased, and their operational lifetimes shortened.

In view of the above it will be understood that there still remains a need to provide further methods for polymer device manufacture where an initially cast or deposited polymer layer is rendered insoluble in the solvent used for subsequent processing steps.

As such, it is an aim of the present invention to provide a new method for polymer device manufacture, preferably that is compatible with high performance. Further it is an aim of the present invention to provide polymer devices obtainable by the new method.

In this regard, the present inventors surprisingly have discovered that a hitherto unknown low concentration of crosslinking moieties (<5 mol %) can successfully be used in a semiconductive layer in device manufacture. The crosslinking moieties can be used either mixed with the semiconductive polymer or as part of the polymer main chain or a side chain, to form a crosslinked polymer product having a low concentration of crosslinked moieties. Further, the present inventors have found that this low concentration of crosslinked moieties substantially does not degrade the performance of the polymer in a polymer device.

As such, in a first aspect of the present invention there is provided a method of forming a polymer device including the steps of:
(i) depositing on a substrate a solution comprising a polymer or oligomer and a crosslinking moiety, to form a layer;
(ii) curing the layer formed in step (i) under conditions so as to form an insoluble crosslinked polymer; characterized in that the crosslinking moiety is present in step (i) at an amount in the range of from 0.05 to 5 mol % based on the total number of moles of the polymer or oligomer and crosslinking moiety in the solution.

The crosslinking moiety may be mixed with the polymer or oligomer in the solution that is deposited in step (i). Alternatively, the crosslinking moiety may be part of the polymer/oligomer main chain or a side chain to the polymer/oligomer in the solution.

The crosslinking moiety is present in the solution in step (i) at a level in the range of from 0.05 to 5 mol %, preferably at a level in the range of from 0.05 to less than 5 mol %, even more preferably in the range of from 0.05 to 3 mol %, still more preferably at a level in the range of from 0.1 to 2 mol % and still more preferably at a level in the range of from 0.1 to 1 mol %, based on the total number of moles of the polymer or oligomer and the crosslinking moiety in the solution.

Where the crosslinking moiety is mixed with the polymer or oligomer in the solution, the level at which the crosslinking moiety is present easily can be measured according to the following formula, $$n_{crosslinker}/(n_{crosslinker}+n_{polymer})\times 100$$

where $n_{crosslinker}$ is the number of moles of the crosslinking moiety, and $n_{polymer}$ is the number of moles of repeat units of the polymer or oligomer. For a random or alternating copolymer that can be written according to the formula $A_xB_yC_{(1-x-y)}$; and for a block copolymer that can be written according to the formula $A_xB_yC_z$, the repeat units of the polymer are defined to be A, B, and C for the purpose of the present invention.

In the three examples (a), (b), and (c) shown below, $n_{polymer}$ is (number of moles of A)+(number of moles of B)+(number of moles of C). In each of examples (a), (b) and (c) shown below, $n_{polymer}$ is (6+6+6)=18. By way of example only, if one mole of crosslinking moiety were present in a solution in combination with any one of polymers (a), (b) or (c), the crosslinking moiety would be present at a concentration of $1/(1+18)\times 100=5.26$ mol %.

(a) ABCBBACACCBAACBCBA
(b) ABCABCABCABCABCABC
(c) AAACCCBBBCCCAAABBB

The relative numbers of crosslinker moiety and repeat units can be measured by microanalysis or by NMR.

Where the crosslinking moiety is part of the polymer or oligomer main chain or side chain, for the purposes of the present invention, the level at which the crosslinking moiety is defined to be present should be measured as indicated below.

Considering the polymer or oligomer to include a repeat unit having one of the following structures:

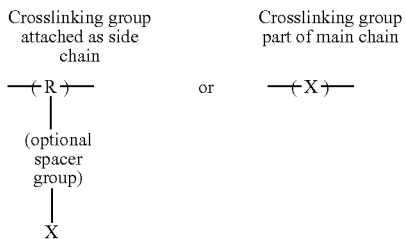

where R is a repeat unit in the main chain of the polymer or oligomer comprising a hydrocarbon and X is a crosslinking moiety, then the level at which the crosslinking moiety is present should be measured as:

$$n_{crosslinker}/(n_{crosslinker}+n_{polymer})\times 100$$

where $n_{crosslinker}$ is the number of moles of the crosslinking moiety X, and $n_{polymer}$ is the number of moles of repeat units of the polymer or oligomer.

The insoluble crosslinked polymer formed in step (ii) will contain 0.05 to 5 mol % crosslinked moieties. Preferably, the crosslinked moieties are present in an amount in the range of from 0.05 to less than 5 mol %, more preferably in an amount of from 0.05 to 3 mol %, even more preferably at an amount in the range of from 0.1 to 2 mol %, still even more preferably at an amount in the range of from 0.1 to 1 mol % based on the total number of moles of the insoluble crosslinked polymer in the layer formed in step (ii).

Considering the insoluble crosslinked polymer to include a repeat unit having one of the following structures:

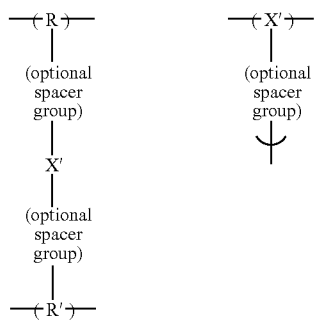

where R and R are repeat units in the main chain of the crosslinked polymer and X is a crosslinked moiety, then the level at which the crosslinked moiety is present should be measured as:

$$n_{crosslink}/(n_{crosslink}+n_{polymer})\times 100$$

where $n_{crosslink}$ is the number of moles of the crosslinked moiety X', and $n_{polymer}$ is the number of moles of repeat units of the polymer.

The present method provides a simple route for crosslinking a polymer film post-deposition to obtain any desired film thickness, for example from about 1 nm to about 500 nm in one process cycle. This is a highly versatile and general process. In the present method, this can be achieved in a number of cases without introducing a significant concentration of charge-carrier traps or exciton traps. As a result, it is possible to fabricate a wide range of practical polymer-polymer heterostructures and incorporate them advantageously into polymer devices, particularly in light-emitting diodes, photodiodes and field-effect transistors. The present method also opens up new avenues for the patterning of polymer films.

In overview, practical and essentially unlimited multilayer stacks and patterned polymer films can be fabricated using a general strategy as defined by the present method.

Unexpectedly, the present inventors have found that crosslinking at this low level substantially does not produce "killer" defects or by-products that severely cripple the electrical and optoelectronic functions of the semiconductive polymer layers.

Curing in step (ii) may be achieved by electron-beam radiation. However, preferably, the curing conditions comprise exposure to short wavelength radiation in an inert atmosphere, more preferably exposure to deep UV radiation in an inert atmosphere. Further preferably, the wavelength of deep ultraviolet radiation is in the range 200 nm to 400 nm, more preferably 245 nm to 370 nm, still more preferably 250 nm to 260 nm. A particularly preferred wavelength is about 254-nm, obtainable from a Hg low-pressure lamp, and 248 nm, obtainable from a KrF excimer laser for example. As such, it is preferred that the crosslinking moiety is sensitive to short wavelength radiation of the afore-mentioned wavelengths.

Where the solution that is deposited in step (i) contains oligomers, curing in step (ii) will polymerise as well as crosslink the oligomers to form the insoluble crosslinked polymer.

Advantageously, it has been found that semiconductive polymers are in general stable to practical deep UV doses required for exposure, as long as exposure is carried out in an inert atmosphere.

The present inventors have found that many major semiconductive polymers (polythiophenes, polyarylvinylenes, polyfluorenes and their copolymers) fortuitously share a common transparency window in the deep ultraviolet at approximately 200-300 nm. This spectral property is well matched to the sensitivity spectra of the preferred crosslinking moieties, discussed below, and also advantageously to commercially-available light sources.

A preferred crosslinking moiety comprises a fluorinated aryl azide. It is further preferred that there are no hydrogen atoms positioned ortho to the azide in the fluorinated aryl azide. To this end, in some embodiments, it may be preferable to position a fluorine atom in any positions that are ortho to the azide.

More preferably, the crosslinking moiety comprises a perfluoroaryl azide, still more preferably a perfluorophenyl azide or perfluoronaphthyl azide.

In a first embodiment, a particularly preferred crosslinking moiety is mixed with the polymer or oligomer in the solution in step (i) and, advantageously, crosslinking proceeds via a mechanism whereby the crosslinking reaction involves a bond-forming reaction between the crosslinking moiety and the polymer or oligomer units, as distinct from a bond-forming reaction between the crosslinking moieties themselves. In other words, in step (ii) the crosslinking moiety substantially does not self-couple or self-polymerise. The present inventors have found that crosslinking moieties having the afore-mentioned capabilities advantageously can be used at a considerably lower concentration.

It is to be noted that the preferred crosslinking moieties as described above substantially do not self-couple or self-polymerise in step (ii). However, such crosslinking moieties may have the capability to self-couple or self-polymerise. It simply is required in one embodiment of the present invention that they substantially do not do so in step (ii) of the present method.

A further preferred crosslinking moiety in this first embodiment has a general formula I:

I where $Ar_F$ comprises a substituted or unsubstituted fluorinated aryl group.

A more preferred crosslinker has a general formula II:

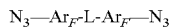

II where $Ar_F$ and $Ar_F'$ independently each comprise a substituted or unsubstituted fluorinated aryl group and L comprises an optional divalent or multivalent linker group. Preferred substituents include substituents that are more bulky than F, e.g. $CF_3$. In one embodiment it is preferred that one or both of $Ar_F$ and $Ar_F'$ has at least one (preferably one) substituent that is more bulky than F.

Preferred linker groups comprise an electron-withdrawing moiety bonded to Ar and/or $Ar_F'$. Such electron-withdrawing moieties include —CO—, —C(O)O—, S(O)$_2$O—, C(O)NR—, or S(O)$_2$NR—, where R is H or a substituent, together with a flexible spacer group such as $(CH_2)_x$ (x=1-5), $(CH_2)_x$—O—$(CH_2)_x$ (x=1-3), or cyclohexadiyl segments. The linker group may comprise two electron-withdrawing moieties (one bonded to $Ar_F$ and the other bonded to $Ar_F'$) that are linked by a flexible spacer group. More preferred linker groups include —C—O—, —C(O)O—$(CH_2)_n$—O(O)C— (n=1-5) and, —C(O)O-cyclohexadiyl—O(O)C—, and —S(O)$_2$—NR—$(CH_2)_x$—NR—S(O)$_2$—.

In general formula II, more preferably $Ar_F$ and $Ar_F'$ each comprises a substituted or unsubstituted fluorinated phenyl or naphthyl group, still more preferably a substituted perfluorophenyl or perfluoronaphthyl group. Most preferably, $Ar_F$ and $Ar_F'$ each comprises a perfluorophenyl group. For the reasons discussed below in relation to compounds XVI to XVIII, in one embodiment, one or more (preferably one) of the fluorine groups on the perfluorophenyl or perfluoronaphthyl advantageously can be replaced with a more bulky group such as a fluorinated alkyl group (e.g. a trifluoromethyl group). This replacement advantageously can be made at the 2 position. Therefore, in one embodiment $Ar_F$ and/or $Ar_F'$ preferably comprises:

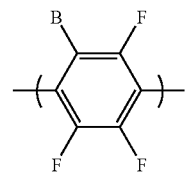

where B is a bulky substituent group such as a fluorinated alkyl group (e.g. a trifluoromethyl group).

The linker group between the perfluorophenyl groups or perfluoronaphthyl groups preferably is a short linker group of the type described above.

Each azide group (—$N_3$) photochemically decomposes to the electron-deficient nitrene which inserts readily into C—H bonds, particularly alkyl C—H bonds: —N+—C—H=—C—N(H)—. As such, each end of the bisazide attaches to a C—H fragment. The two C—H fragments nominally belong to adjacent polymer chains or oligomers and so a crosslink is formed between these. It is for this reason that the polymer or oligomer preferably comprises a plurality of saturated hydrocarbon segments. However, often saturated hydrocarbons, and specifically alkyl C—H, already will be present in the polymer or oligomer in order to improve solubility.

The inventors have discovered that the crosslinking proceeds through a highly efficient insertion into C—H bonds, particularly alkyl C—H bonds, without generally destroying pi-conjugation present on the main chain. Further, the ability of the crosslinking moiety to form bonds with the polymer or oligomer has been found by the present inventors to enable lower concentrations of crosslinking moiety to be used.

The present inventors have found by experiments that this crosslinking moiety does not generally suffer from the drawback of leaving residues that may interfere with the properties (such as charge-transport and luminescence properties) of the polymer.

Furthermore, the crosslinking mechanism of this crosslinking moiety has been found to be generally compatible with the presence of pi-conjugation in a semiconductive polymer.

Furthermore, it has been found that the solid-state crosslinking efficiency for conjugated polymers is unexpectedly high (>80%) with this crosslinking moiety. Without wishing to be bound by theory, the high efficiency of this class of crosslinkers is thought to be due to the presence of fluorine atoms on the ring (particularly the ortho-positioned fluorines) which suppresses a competing parasitic ring expansion side-reaction.

The following novel crosslinkers have been synthesized by the present inventors. These crosslinker groups are suitable for mixing with a polymer or oligomer in a solution:
alkylene diol bis(4-azido-2,3,5,6-tetrafluorobenzoate),
alkylene diamine bis(4-azido-2,3,5,6-tetrafluorobenzamide),
alkylene diamine bis(4-azido-2,3,5,6-tetrafluorobenzenesulfonamide),
cycloalkylene diol bis(4-azido-2,3,5,6-tetrafluoro-benzoate),
cycloalkylene diamine bis(4-azido-2,3,5,6-tetrafluoro-benzamide),
cycloalkylene diamine bis(4-azido-2,3,5,6-tetrafluoro-benzenesulfonamide), Specific examples of these novel crosslinkers include:
ethylene diamine bis(4-azido-2,3,5,6-tetrafluorobenzamide);
ethylene diamine bis(4-azido-2,3,5,6tetrafluoro benzenesulfonamide)
1,3-cyclohexane diol bis(4-azido-2,3,5,6-tetrafluoro-benzoate)
1,4-cyclohexane diol bis(4-azido-2,3,5,6-tetrafluoro-benzoate)

Equivalents of the above-mentioned novel crosslinkers where at least one (preferably one) of the fluorines in the tetrafluorobenzamide, tetrafluorobenzene sulphonamide or tetrafluorobenzoate is replaced by a more bulky group (such as a fluorinated alkyl group, e.g. $CF_3$) are desirable. Replacement preferably is at the 2 position.

Crosslinkers having general formula II:

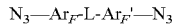   II

Where $Ar_F$ and $Ar_F'$ each is as defined above may be synthesized by a method comprising the step of reacting F—$Ar_F$-L-$Ar_F'$—F with an azide.

Preferably, the azide is a metal azide, more preferably an alkali metal azide, still more preferably sodium azide.

F—$Ar_F$-L-$Ar_F'$—F may be made by reaction of the appropriate fluorinated aryl (e.g. pentafluorophenyl) acid halide. The co-reactant will depend on the nature of L. However, the reaction of a fluorinated aryl (e.g. pentafluorophenyl) acid chloride with a diol or diamine will be generally useful.

For example, F—$Ar_F$-L-$Ar_F'$—F may be made by reacting F—$Ar_F$—COX or F—$Ar_F$—$SO_2$X (X=Cl, Br) with HO—R—OH or NHY—R—NHY (Y=H, alkyl, or aryl, preferably alkyl or aryl for improved solubility in the final product) (R=alkylene, cycloalkylene) to form F—$Ar_F$-L-$Ar_F'$—F.

In the case of ethylene diol bis(4-azido-2,3,5,6-tetrafluorobenzoate), this may be made by reacting 1 mole equivalent of ethylene diamine with a slight excess of 2 mole equivalents of pentafluorobenzyl chloride to produce ethylene diamine bis(pentafluorobenzoate). The ethylene diol bis(pentafluorobenzoate) then may be reacted with a slight excess of 1 mole equivalent of the metal azide to produce ethylene diol bis(4-azido-2,3,5,6-tetrafluorobenzoate).

In the case of ethylene diamine bis(4-azido-2,3,5,6-tetrafluorobenzenesulfonomide), this may be made by reacting 1 mole equivalent of ethylene diamine with a slight excess of 2 mole equivalents of pentafluorobenzenesulfonyl chloride to produce ethylene diamine bis(pentafluorobenzenesulfonamide). The ethylene diamine bis(pentafluorobenzenesulfonamide) then may be reacted with a slight excess of 1 mole equivalent of a metal azide to produce ethylene diamine bis(4-azido-2,3,5,6-tetrafluorobenzenesulfonamide).

Referring to step (i), desirably the solution will comprise a blend/mixture of the polymer and the crosslinking moiety. However, in another embodiment, the solution may instead contain a polymer or oligomer where the crosslinking moiety is bound to the polymer or oligomer, typically as a side group.

In this embodiment, a particularly preferred crosslinking moiety is part of the main chain of the polymer or oligomer or is attached as a side chain to the polymer or oligomer and advantageously, crosslinking proceeds via a mechanism whereby the crosslinking reaction involves a bond-forming reaction between the crosslinking moiety and the polymer or oligomer units, as distinct from a bond-forming reaction between the crosslinking moieties themselves. In other words, in step (ii), the crosslinking moiety substantially does not self-couple or self-polymerise.

In this embodiment, preferred structural units in the polymer or oligomer comprising a crosslinking moiety have a general formula III or IV:

where $Ar_F$ comprises a substituted or unsubstituted fluorinated aryl group and R is a structural unit (typically a repeat unit) in the main chain of the polymer or oligomer.

These preferred crosslinking moieties comprise an azide group and, as such, these crosslinking moieties have the same advantages as described above in relation to the first embodiment of preferred crosslinkers according to the present invention.

In general formula III and IV, $Ar_F$ can be as defined anywhere above in relation to general formula II.

In general formula III and IV, preferably $Ar_F$ comprises a substituted or unsubstituted fluorinated phenyl or naphthyl group, more preferably a perfluorophenyl or perfluoronaphthyl group. Most preferably, $Ar_F$ comprises a perfluorophenyl group.

Referring generally to the present method, deposition in step (i) may be for example by any suitable solution-processing method. In this regard, inkjet printing, spin casting, screen-printing, dip coating, and flexographic printing may be mentioned.

A suitable material for the substrate will depend on the polymer device being formed. For LEDs and photodiodes/photodetectors. Preferred substrates include a layer of ITO-on-glass, ITO-on-PET, ITO-on-Si etc. For FETs, preferred substrates include a layer of glass, PET, polycarbonate etc. The substrate may itself comprise a laminate structure. In other words, the substrate may itself comprise a plurality of different layers.

As mentioned above, in step (ii) of the present method, the layer formed in step (i) is rendered insoluble. In order to achieve this insolubility, a sufficient degree of crosslinking must occur during step (ii) when the layer formed in step (i) is subjected to crosslinking conditions. The precise amount, within the specified range, of crosslinking moiety needed in the solution that is deposited in step (i) in order to achieve the required degree of crosslinking in step (ii) will depend on the molecular weight distribution characteristics of the polymer. Generally, the higher the molecular weight of the polymer, the lower the amount of crosslinker that is needed. The minimum amount required suitably can be determined by a gel-fraction experiment. This experiment simply may be carried out as follows:

blend the polymer or oligomer at a test concentration in an appropriate solvent (for example 0.5-2.5 wt % in an aromatic hydrocarbon solvent) with the crosslinking group at a concentration in the range of from 0.05-5 mol % based on the total number of moles of crosslinking group and polymer/oligomer in the solution; or synthesise the polymer with the said fraction of crosslinking moieties.

cast a film by spin coating or ink-jet printing and then cure;

measure thickness by profilometry, ellipsometry or interferometry;

expose the film to the crosslinking radiation at a dose of 100 mJ/cm$^2$.

soak (or develop) the film for 10 s in a solvent that normally dissolves the polymer, then blow-dry or spin-off the solvent;

measure the film thickness a second time;

repeat the above sequence at different crosslinking moiety molar ratios until insolubility and the desired thickness is retained.

A preferred range for the concentration of the polymer or oligomer in the solution is 0.5 to 2.5 wt % before addition of the crosslinking moiety.

The crosslinked polymer formed in step (ii) advantageously may be a conductive, semiconductive or insulating polymer. Preferably, the crosslinked polymer is a semiconductive polymer.

Where a polymer is present in the solution used in step (i) and the crosslinking moiety is mixed with the polymer, desirably, the polymer in the solution may be a conductive, semiconductive or insulating polymer. Preferably, the polymer in the solution in step (i) is a semiconductive polymer. Where the polymer in the solution is a semiconductive polymer, curing the layer in step (ii) advantageously substantially does not affect the semiconductive properties of the polymer.

In contrast to a semiconducting polymer, a conducting polymer typically is heavily doped (>5 mol % by repeat unit) to a conductive state. As a result, a conducting polymer typically has a charge carrier concentration of >$10^{18}$ cm$^{-3}$. By 'conducting polymer' is typically meant a polymer having a conductivity >$1 \times 10^{-5}$ S/cm. As such, their electrical properties are essentially insensitive to additional impurities. Such conducting polymers are useful mainly as transmission lines or electrode contacts. Crucially they often possess a transmission window that extends greatly over portions of the optical, ultraviolet and deep ultraviolet spectral regions, with increased laxity for photopatterning processes.

Semiconductive polymers typically are undoped or intrinsically doped at a low concentration (typically 0.001 mol % or less). In contrast to a conducting polymer, a semiconductive polymer typically has a charge carrier concentration of <$10^{15}$ cm$^{-3}$. By 'semiconductive polymer' is typically meant a polymer having a conductivity <$1 \times 10^{-8}$ S/cm. These polymers crucially form the core of a wide range of polymer device technologies including LEDs, FETs and PVs. They typically have fairly narrow transmission windows in the optical-ultraviolet region as explained above. They also have important and unique transport and photophysical properties that are far more sensitive to impurity levels.

The inventors have found that semiconductor polymers can be crosslinked in accordance with the present invention with substantially no loss in function.

In particular, the present inventors have found that the crosslinking moiety has practically no effect on the photoluminescence and electroluminescence properties of a wide range of conjugated polymer films particularly when used in an amount in the range of from 0.1-0.5 mol %) and when the molecular weight of the polymer is sufficiently high (>300,000).

The inventors have found that the crosslinking moiety and the crosslinking methodology as described in this invention are in fact compatible even with wide bandgap materials, in particular blue EL polymers, for example as described in WO 03/095586. The process does not introduce exciton or charge traps that would have otherwise impaired the device performance of these particularly sensitive materials.

For lower-molecular-weight materials, a higher concentration of the crosslinking moiety needs to be used (>0.5%), and in some cases, this will begin to have a deleterious effect of the photoluminescence efficiency of the polymers, as shown in FIG. 11 for the crosslinking moiety ethylene diol bis(p-azido-2,3,5,6-tetrafluorobenzoate). In a number of cases, the photoluminescence efficiency can be partially recovered by annealing.

Polymer XI:

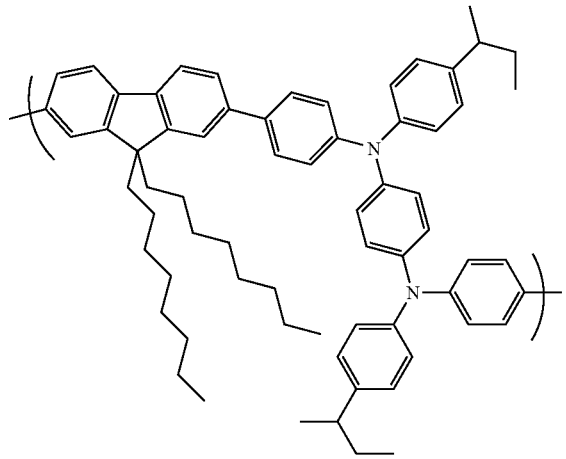

Polymer XII:

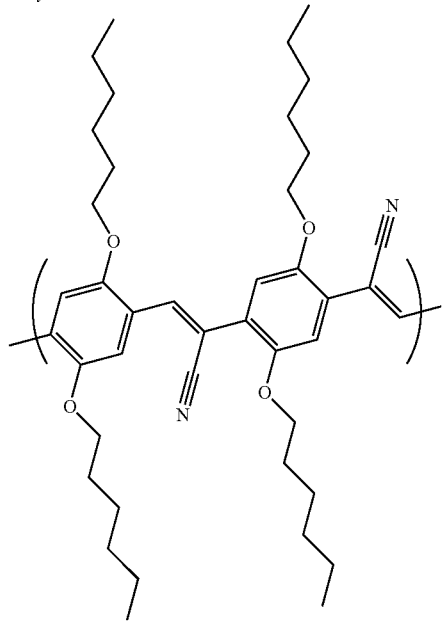

Crosslinking moiety:

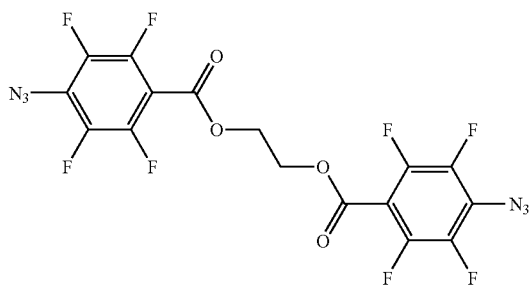

Exposure conditions: 254-nm Hg line; 1 mW/cm$^2$, 2 min

The undesirable impart of the crosslinking moiety at high concentrations can be further minimised by increasing the steric bulk on the crosslinking moiety. In the case of a crosslinking moiety of general formula II, this can be achieved for example by appropriate selection of L, or substituents on $Ar_F$, $Ar_F'$ and/or L. For example, the following series is observed with respect to photoluminescence quenching:

XVI > XVII > XVIII

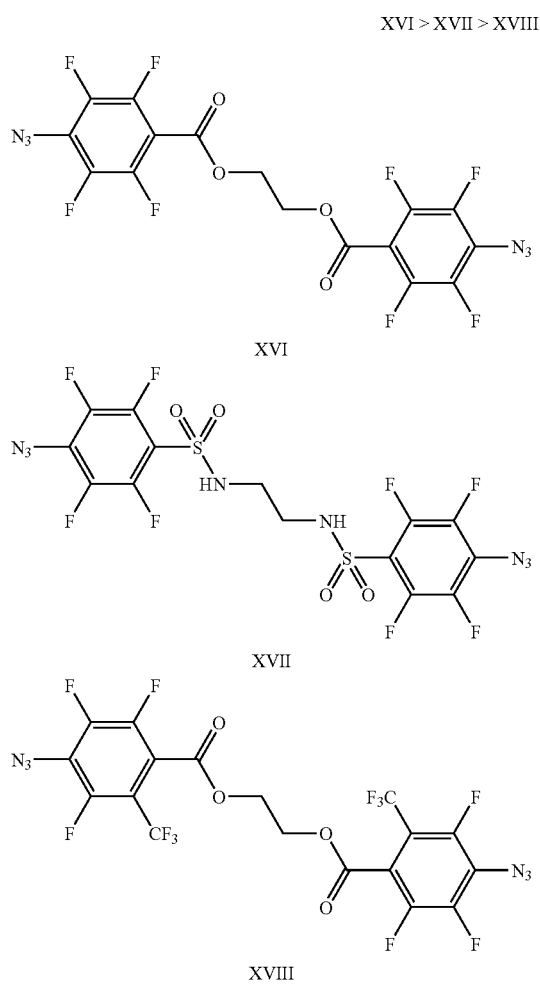

Therefore if the crosslinking moiety is required to be present at a high concentration due to a low molecular weight of the polymer to be crosslinked, and as a result photoluminescence quenching becomes an issue, a crosslinking moiety with higher steric bulk near the perfluorinated ring, for example a 2-trifluoromethyl substituted compound XVIII, can be chosen to alleviate or completely suppress the problem.

This demonstrates the versatility of the fluorinated phenyl azides in providing an effective crosslink for a wide range of conjugated polymers without impairing the desirable photophysical and electronic properties of the polymers.

Preferably the polymer or oligomer backbone is at least partially conjugated. Further, in one embodiment it may be preferable for the polymer or oligomer backbone to be substantially or even fully conjugated.

Referring to the structure of the polymer or oligomer, preferably this comprises a plurality of saturated hydrocarbon segments (—$CH_2$— and —CH—) in the side chain or main chain. It is preferred that the polymer or oligomer comprises a plurality of aliphatic hydrogens.

A preferred weight fraction of these segments in the polymer or oligomer is 10-100%, for a semiconductive polymer a preferred weight fraction is 10-70%.

Preferred crosslinked semiconductive polymers comprise a repeat unit $Ar_1$ comprising:

(1) substituted or unsubstituted phenylene or arylvinylene, such as p-phenylenevinylene;

(2) 9,9-disubstituted fluorene, such as 9,9-dialkylfluorene (which may be further substitutued);

(3) substituted or unsubstituted triarylamine;

(4) unsubstituted or substituted heteroaromatic units such as thiophenes, benzothiadiazoles, quinolines, pyridines, preferably the substituted analogs; or (5) unsubstituted or substituted oxadiazole.

Preferred substituents include alkyl, cycloalkyl, alkoxy, aryl, and aryloxy groups.

The polymer may further contain one or more co-repeat units in combination with $Ar_1$. Preferred co-repeat units comprise p-linked unsubstituted or substituted phenylene; unsubstituted or substituted phenylenevinylene; 2,5-linked substituted or unsubstituted benzothiadiazole; 2,5-linked substituted or unsubstituted thiophene; bithiophene or terthiophene, substituted or unsubstituted triarylamine or bis(triarylamine). It is particularly preferred that the crosslinked polymer contains one or more co-repeat units when $Ar_1$ comprises 9,9-disubstituted fluorene.

All of these polymers can be crosslinked in accordance with the present invention.

Of course, the polymer or oligomer must be soluble in order for it to be in solution in step (i). To this end, the polymer or oligomer may include solubilising groups. Preferred solubilising groups include alkyl, alkoxy aryl, cylcoalkyl, aryloxy, and cylcoalkyloxy groups.

It is preferred that the crosslinking moiety has an absorption in the narrow transmission window in the deep ultraviolet. Typically, this will be in the range 200 nm to 300 nm, more preferably 245 to 270 nm, even more preferably 250 nm to 260 nm. The absorption of a crosslinking moiety can be measured by UV visible absorption spectroscopy.

It is advantageous for the crosslinking moiety to have the appropriate absorption in this range because this corresponds to a transition window common for a number of semiconductive polymers. Therefore, crosslinking and imaging of the polymer can be accomplished at low exposure doses.

Preferred thicknesses for the cured layer formed in step (ii) are in the range of 500 nm or less. Where curing in step (ii) is by exposure to UV radiation, the insoluble layer formed can be from 500 nm thick down to few nm thick after one appropriate UV exposure. Layers where the final thickness is greater than 500 nm, where necessary, may be fabricated by repeated coating and curing. The required final film thickness depends on end-use application. There is in principle no limit to the number of layers that can be fabricated by this method.

The desired thickness of the insoluble layer formed in step (ii) will be dependent, to some extent, on the function of the layer. Where the layer is an injection interlayer in a polymer LED, a preferred thickness is in the range of from 5 to 20 nm. Where the layer is a charge-transport layer, in a photodiode for example, a preferred thickness is in the range of from 10 to 50 nm. Where the layer is a cladding layer in a waveguide device, a preferred thickness is in the range of from 100 to 400 nm. Where the layer is the channel layer in an FET, a preferred thickness is in the range of from 20 to 300 nm.

In one embodiment the layer deposited in step (i) may be a polymer blend or composite. Crosslinking may be used advantageously to increase the thermal stability of the cured polymer blend or composite or to optimise resistance of the final cured layer to solvent dissolution.

Referring to the conditions for curing in step (ii), where curing comprises exposing the layer to ultraviolet radiation this is preferably at a power of 1-100 mW/cm$^2$, and preferably exposure time is in the range of about 0.1-100 s. The energy dose on the layer to be cured is preferably 1-100 mJ/cm$^2$, more preferably 5-20 mJ/cm$^2$.

The layer is cured in step (ii) so that it is rendered insoluble. This means that the layer, and thus, the polymer does not dissolve completely in any solvent that the layer would have dissolved in, prior to crosslinking. As mentioned above, achieving this result depends on achieving the required level of crosslinking for the particular layer in question. Generally, the cured layer will be is rendered insoluble in common organic solvents. Further, generally, the layer will be rendered insoluble in aromatic hydrocarbon solvents, including, toluene, xylene, mesitylene, durene, hydronaphthalene, etc, and halogenated solvents like chloroform, chlorobenzene etc. These solvents thus are rendered useable in subsequent processing during device manufacture.

One specific test for determining insolubility may be described as follows:
- cast a film by spin coating or ink-jet printing and then cure;
- accurately measure thickness by profilometry, ellipsometry or interferometry, call this $d_1$;
- soak (or develop) the film for 10 s in a solvent that normally dissolves the polymer, then blow-dry or spin-off;
- measure the film thickness a second time, call this $d_2$.

When the layer is totally "insoluble" there should be no decrease in film thickness after soaking the film/layer (i.e. $d_2/d_1=1.0$). In many instances, however, the layer only needs to be partially insoluble. Provided that the fraction retained ($d_2/d_1$) is known, any decrease can be allowed for in the design of the device. In general however, $d_2/d_1$ needs to be greater than 0.4, preferably greater than 0.5 to be useful.

Generally, after curing in step (ii) the layer may be contacted with a solvent. The fact that the crosslinked polymer is insoluble in solvents in which an equivalent uncrosslinked polymer would have been soluble means that the solvent with which the layer is contacted may be selected from a wide class of solvents including common organic solvents. This contact will not dissolve the crosslinked polymer that was formed in step (ii).

Optionally, after curing in step (ii), the layer may be washed with a suitable solvent. Such a washing step would be included where the layer is subjected in step (ii) to patterned crosslinking. This would involve exposing only selected areas of the layer from step (i) to the curing conditions in step (ii). This may be achieved for example by exposure to UV-radiation through a mask. Material in the exposed area will become insoluble whereas material in the unexposed area will remain soluble. This enables material in the unexposed are to be removed in the washing step.

Optionally, after curing in step (ii), the layer may be chemically modified by suitable chemical reaction by wet chemistry. Such chemical reactions may include aromatic sulfonation, aminomethylation, or other derivatisation reactions.

Sulfonation introduces $SO_3H$ groups into a fraction of the polymer repeat units. This can be used to fabricate a self-doped conductive polymer layer, for example. This particular reaction can be carried out under a wide variety of conditions, for example, by reacting the layer at −60° C. with a dilute chloroform solution of chlorosulfonic acid.

Another reaction that may be useful is a methylation reaction of the NH groups introduced by the crosslinking reaction. This reaction will replace the hydrogen atom with a potentially more stable methyl group. This particular reaction can be carried out by reacting the layer at room temperature with methyl iodide, and then washing with triethylamine in a chloroform-ethanol mixture. Therefore after rendering the polymer layer insoluble, a variety of chemical reactions can be carried out to alter or tune the bulk properties and surface properties of the layers.

A further (second) layer may be deposited on the layer formed by the present method. In this regard, in view of the curing in step (ii), the layer formed in the present method will not be soluble in any solution used to deposit a further (second) layer.

Optionally, the present method may further include a step of annealing the insoluble polymer formed in step (ii) of the method according to the first aspect of the present invention. Annealing may be as described below in accordance with the sixth aspect of the present invention.

Typically, the polymer device in the method according to the first aspect of the present invention is an optical device. Preferably, the device is a polymer light emitting device, a polymer transistor such as a field effect transistor, a photodetector, a photovoltaic device, a waveguide device, or a distributed Bragg reflector.

Polymer LED devices may be fabricated with a crosslinked hole-transport polymer layer deposited by the method of the present invention. The devices further may include a light-emitting polymer layer and/or electron-transport polymer layer and/or exciton-block polymer layer. Optionally these further layers could be deposited according to the present method. For polymer LEDs, one may for example conceive of a structure which comprises a hole-injecting and electron-blocking polymer layer formed on the anode, followed by the light-emitting polymer layer, and then an electron-injecting, hole-blocking and exciton-blocking polymer layer, followed by the cathode. Advantageously appropriate polymers can also be patterned as the light-emitting layer to give a full colour display as discussed above. In addition, the light-emitting layer can be a film of a crosslinked blend of polymers.

Polymer waveguide LED devices may be fabricated with one or more crosslinked polymer cladding layers deposited by the method of the present invention. The devices further include a core light-emitting layer which optionally may be deposited in accordance with the present method. A waveguide device is characterized by a core layer (or strip) having a higher refractive index than the adjoining clad layers (or surrounding). The core layer and clad layers may each comprise of one or more individual layers. Light of the appropriate wavelength that satisfies a phase-matching condition is trapped by total internal reflection and guided in the core layer (or strip) on account of its higher refractive index. This light can then be emitted at the edge of the device or guided to another region where it can be out-coupled. The light emitted in this way can be highly directional and also be well coupled to optical fibres.

Polymer distributed Bragg reflectors may be fabricated with crosslinked alternating high refractive index and low refractive index polymer multilayers deposited by the method of the present invention. A Bragg reflector comprises a plurality of quarterwave-thick ($d_H$, $d_L$) layers of high ($n_H$) and low ($n_L$) refractive index materials. Light of wavelengths that satisfy the Bragg condition ($\lambda/2 = n_H d_H + n_L d_L$) is strongly reflected within the stack. The Bragg reflector can be coupled with another Bragg reflector or mirror to form an optical resonator. Such resonators have important uses as wavelength selectors.

Polymer microcavity LED devices may be fabricated with one or more crosslinked polymer distributed Bragg reflector layers deposited by the method of the present invention. The devices further may include a core light-emitting layer. Optionally, the core light-emitting layer may be deposited in accordance with the present method.

Polymer FET devices may be fabricated with a crosslinked semiconductive polymer layer deposited by the method of the present invention. The devices further may include a crosslinked insulative polymer layer. Optionally, the insulative polymer layer may be deposited according to the present method. This is particularly if this layer is deposited before the semiconductive layer. The devices may be in top-gate, side-gate or bottom-gate configuration. For polymer FETs, one may for example conceive of a structure which comprises of a charge transporting semiconductive polymer formed on a substrate between source and drain electrodes, followed by an insulative polymer that acts as the gate insulator. This insulative polymer layer can be deposited from the same solvent system used to deposit the semiconductive polymer after the latter is crosslinked.

Polymer photovoltaic devices may be fabricated with a photoresponsive layer comprising a crosslinked polymer blend or polymer composite.

A second aspect of the present invention provides a polymer device obtained or obtainable by the method as defined anywhere in relation to the first aspect of the present invention. The device may be as defined anywhere in relation to the first aspect of the present invention. In any of the devices described above in relation to the first aspect of the present invention and in devices according to the second aspect of the present invention, preferred materials for the cathode include alkali earth metals, such as barium and calcium.

A third aspect of the present invention provides the use of a polymer device according to the second aspect of the present invention.

A fourth aspect of the present invention provides a solution containing a polymer or oligomer and a crosslinking moiety characterized in that the crosslinking moiety is present in an amount in the range of from 0.05 to 5 mol % based on the total weight of the polymer or oligomer and the crosslinking moiety in the solution.

In the fourth aspect of the present invention, the polymer or oligomer, the crosslinking moiety and the solvent may be as described anywhere above in relation to the first aspect of the present invention. Furthermore, the concentrations thereof in the solution may be as described anywhere above in relation to the first aspect of the present invention.

Preferably the crosslinking moiety is mixed with the polymer or oligomer. A preferred solution according to the fourth aspect of the present invention contains a semiconductive polymer. In one particularly preferred embodiment, the crosslinking moiety has general formula II where $Ar_F$ and $Ar_F'$ each is a perfluorophenyl group.

A fifth aspect of the present invention provides the use of a solution according to the fourth aspect of the present invention in the manufacture of a polymer device as defined in accordance with the first and second aspects of the present invention.

A sixth aspect of the present invention provides a method of forming a polymer device comprising the steps of:
(i) depositing on a substrate a solution comprising a polymer or oligomer and a crosslinking moiety to form a layer;
(ii) curing the layer formed in step (i) under conditions to form an insoluble crosslinked polymer;
(iii) annealing the insoluble polymer formed in step (ii); and
(iv) optionally chemically modifying the surface or bulk of the insoluble polymer formed in step (ii).

In the method according to the sixth aspect of the present invention, the polymer, oligomer, crosslinking moiety and concentrations thereof and the crosslinking conditions preferably may be as defined anywhere in relation to the first aspect of the present invention. In the sixth aspect of the present invention, it is not essential for the crosslinking moiety to be present in step (i) in an amount in the range of from 0.1 to 5 mol %.

Preferably, annealing in step (iii) is carried out at a temperature in the range of 120 to 200° C.

In relation to the sixth aspect of the present invention, the present inventors surprisingly have discovered that an annealing step after film deposition and crosslinking can advantageously at least partially recover any observed degradation of properties that occur during step (ii).

Chemical modification in step (iv) of the method according to the sixth aspect of the present invention may be carried out as defined in relation to the first aspect of the present invention.

The present invention now will be described in further detail with reference to the attached figures in which.

EXAMPLES

Synthesis of Crosslinkers

Figure 1:
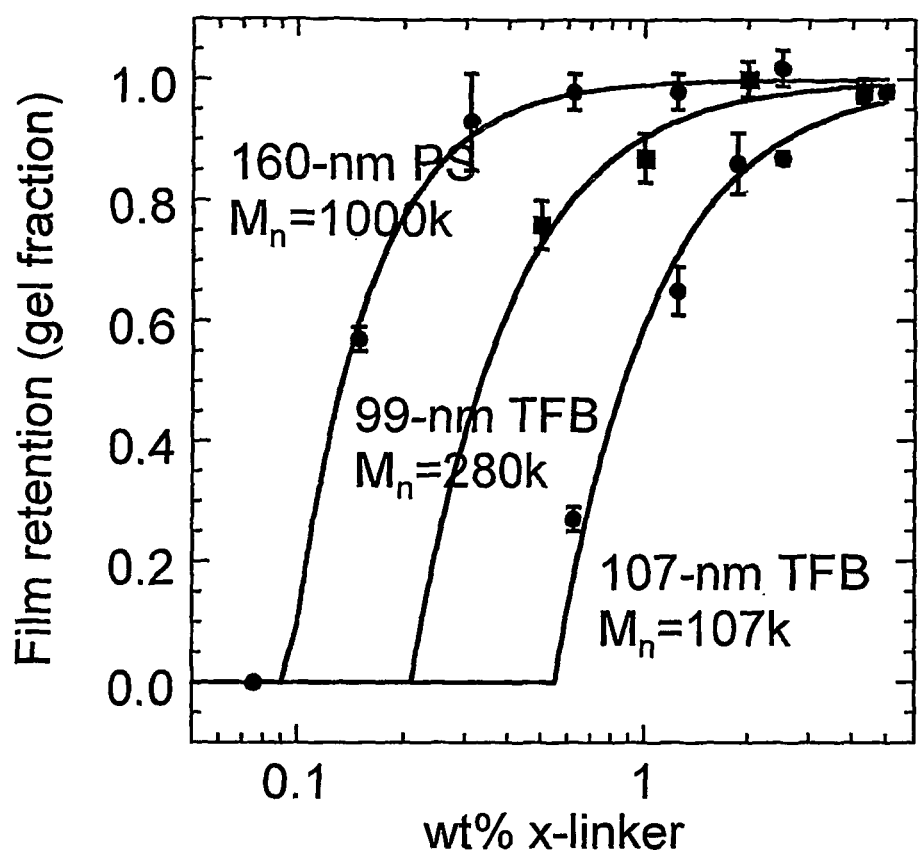
FIG. 1 shows typical film retention (or gel point) characteristics at different crosslinker ratios.

The following synthetic scheme is used: a diol or diamine is reacted quantitatively with the appropriate pentafluorophenyl acid halide in the presence of an acid scavenger, and the product then reacted quantitatively with sodium azide to yield the bis(perfluorophenyl azide) crosslinkers after recrystallisation.

Example 1 ethylene glycol bis(4-azido-2,3,5,6-tetrafluoro benzoate)

Ethylene glycol (135 mg, 2.1 mmol) and triethylamine (510 mg, 5.0 mmol), together dissolved in 10 mL anhydrous ether is added to pentafluorobenzoyl chloride (1.2 g, 5.0 mmol) in 10 mL anhydrous ether. White precipitate of triethylammonium chloride is obtained and filtered off. The filtrate is washed with 3×20 mL water, dried with $MgSO_4$, and then evaporated to recover ethylene glycol bis(pentafluorobenzoate) (I) as a colourless liquid (yield, 75%). Sodium azide (150 mg, 2.3 mmol) in 2.2 mL water and 3.7 mL acetone is then reacted with I (500 mg, 1.1 mmol) in 2 mL acetone, and stirred overnight on a 60° C. hotplate. A white precipitate is obtained. The solution is reduced to half-volume by evaporation and the precipitate is filtered off (yield, 80%) and recrystallised twice in 1:3 chloroform-hexane to give ethylene glycol bis(4-azido-2,3,5,6-tetrafluorobenzoate) (II) as white crystals. FTIR: 2134 ($N_3$ asymmetric stretch), 1731 (C=O stretch), 1645, 1483, 1252 ($N_3$ symmetric stretch), no acid OH band at 3000-3500.

Example 2 ethylene diamine bis(4-azido-2,3,5,6-tetrafluorobenzoate)

Ethylene diamine (130 mg, 2.1 mmol) and triethylamine (510 mg, 5.0 mmol), together dissolved in 10 mL anhydrous ether is added to pentafluorobenzoyl chloride (1.2 g, 5.0 mmol) in 10 mL anhydrous ether. White precipitate is obtained and filtered off. The residue is washed with chloroform, then water and then filtered to recover ethylene diamine bis(pentafluorobenzoate) (III) as white needle crystals (yield, 100%). Sodium azide (270 mg, 4.2 mmol) in 1.7 mL water and 4.0 mL DMF is then reacted with III (870 mg, 2.0 mmol) in 20 mL DMF, and stirred overnight on a 60° C. hotplate. A white precipitate is obtained. The solution is reduced to half-volume by evaporation and the precipitate is filtered off (yield, 35%), dried and recrystallised from DMF to give ethylene diamine bis(4-azido-2,3,5,6-tetrafluorobenzoate) (IV) as white crystals. FTIR: 2129 ($N_3$ asymmetric stretch), 1666 (C=O stretch), 1554, 1483, 1242 ($N_3$ symmetric stretch), no acid OH band at 3000-3500.

Example 3 ethylene diamine bis(4-azido-2,3,5,6-tetrafluoro benzenesulfonamide)

Ethylene diamine (70 mg, 1.0 mmol) and triethylamine (240 mg, 2.0 mmol), together dissolved in 8 mL anhydrous chloroform is added to pentafluorobenzenesulfonyl chloride (710 mg, 2.2 mmol) in 2 mL anhydrous chloroform. White precipitate is obtained and filtered off. The filtrate is washed with 3×4 mL half-saturated aqueous KCl, then dried with $MgSO_4$ and evaporated to recover ethylene diamine bis(pentafluorobenzenesulfonamide) (V) as white crystals (yield, 80%). Sodium azide (105 mg, 1.6 mmol) in 1.0 mL water and 4.0 mL acetone is then reacted with V (390 mg, 0.76 mmol), and stirred overnight on a 60° C. hotplate. A white precipitate is obtained. The solution is reduced to half-volume by evaporation and 2 mL water added. The precipitate is then filtered off, dried and recrystallised from chloroform to give ethylene diamine bis(4-azido-2,3,5,6-tetrafluorobenzenesulfonamide) (VI) as white crystals. Soluble in acetone, isopropanol and xylene, but not in water or hexane. FTIR: 3315 (N—H stretch), 2130 ($N_3$ asymmetric stretch), 1642, 1493, 1358 ($SO_2$ asymmetric stretch), 1230 ($N_3$ asymmetric stretch), 1169 ($SO_2$ symmetric stretch), 989, no hydrated acid band at 1650-2800.

Example 4

1,3-cyclohexane diol bis(4-azido-2,3,5,6-tetrafluorobenzoate)

As in Example 1, but with 1,3-cyclohexane diol.

Example 5

1,4-cyclohexane diol bis(4-azido-2,3,5,6-tetrafluorobenzoate)

As in Example 1, but with 1,4-cyclohexane diol.

Example 6 ethylene diol bis(4-azido-2-trifluoromethyl-3,5,6-trifluorobenzoate)

In a similar way, ethylene glycol (2.1 mmol) and triethylamine (5.0 mmol), together dissolved in 10 mL anhydrous ether is added to 2-trifluoromethyl-3,4,5,6-tetrafluorobenzoyl chloride (5.0 mmol) in 10 mL anhydrous ether. White precipitate of triethylammonium chloride is obtained and filtered off. The filtrate is washed with 3×20 mL water, dried with $MgSO_4$, and then evaporated to recover crude ethylene diol bis(2-trifluoromethyl-3,4,5,6-tetrafluorobenzoate). Sodium azide (150 mg, 2.3 mmol) in 2.2 mL water and 3.7 mL acetone is then reacted with I (1.1 mmol) in 2 mL acetone, and stirred overnight on a 60° C. hotplate. The solution is reduced to half-volume by evaporation and the precipitate is filtered off and recrystallised twice in 1:5 chloroform-hexane.

(A) Crosslinking of a Hole-Transport-and-Electron-Blocking Interlayer or Interlayer Stack to Obtain Precise Control Over Interlayer Thickness and Injection Characteristics

Example 1

F8BT-emittter LED a. Photoresist is removed from prepatterned ITO glass substrate using acetone, isopropanol and nitrogen blow-off. The ITO surface is then exposed to an oxygen plasma for 10 min in a barrel etcher (Tegal Barrel Etcher 421; typical conditions: pressure, 450 mbar; power 150 W). Poly(3,4-ethylenedioxythiophene): polystyrenesulfonate (PEDT:PSS) formulated with a PEDT-to-PSS ratio of 1:15 is then spin-cast from an aqueous solution to give a 60-70-nm thick film. The film is baked for 15 min under nitrogen on a hotplate set at 150° C.

b. Poly(9,9-dioctylfluorene-alt-[phenylene-(N-p-2-butylphenyl)imine-phenylene]) (TFB) formulated with 1.8% ethylene glycol bis(4-azido-2,3,5,6-tetrafluorobenzoate) (I) by weight of TFB is then spin-cast from a 0.9 w/v % mixed-xylenes solution under nitrogen to give a 15-nm thick film. The film is then exposed under nitrogen through a photomask to 254-nm deep ultraviolet radiation for 2 min at an illuminance of 1 mW/cm$^2$ on the film surface.

(1. The preferred interlayer polymer at the anode interface has hole-transporting and electron-blocking properties. This polymer also needs be stable without participating in undesirable electrochemical reactions with the light-emitting-polymer that degrades the electrical properties of the interface with operation. Exemplary interlayer polymers include TFB and poly(triarylamines).

(2. The preferred polymer concentration is determined by the desired thickness of the interlayer film, and can be easily found by spinning trials. Typically, for a target interlayer thickness of 10-20 nm, the required polymer concentration is 0.2-1 w/v %, depending on polymer viscosity, and the spin speed required is 2000-8000 rpm. Alternatively metered ink-jet printing may be used.

(3. The preferred crosslinker-to-polymer mol ratio is determined by the number-averaged molecular weight and its distribution of the polymer used. The crosslinker acts by increasing the effective molecular weight of the polymer in the film to the point when it no longer dissolves in solvents. However, low-molecular-weight-species if present do not reach the gel limit and so can still be leached off in good solvents. Therefore, as the crosslinker ratio or the polymer molecular weight is reduced, the fraction of film thickness retained is smaller. Typical film retention (or gel point) characteristics are shown in FIG. 1. For a number-averaged molecular weight of $10^5$, the crosslinker ratio required for reasonable film retention >50% is 1.5-2 w/w %. For a number-averaged molecular weight of $10^6$, the ratio required is 0.3-0.6 w/w %. The ratio chosen should be the minimum required to ensure the desired crosslinking level.

(4. The preferred irradiation dose is 10-100 mJ/cm$^2$. The minimum dose required depends on the intrinsic absorption of the polymer at 254-nm through the filter effect. It can be determined easily by dose series trials.

(5. The preferred wavelength of irradiation is 254-nm or 248-nm. This is conveniently obtained from a low-pressure mercury lamp source (254-nm) or KrF excimer laser source (248-nm).

Figure 2:
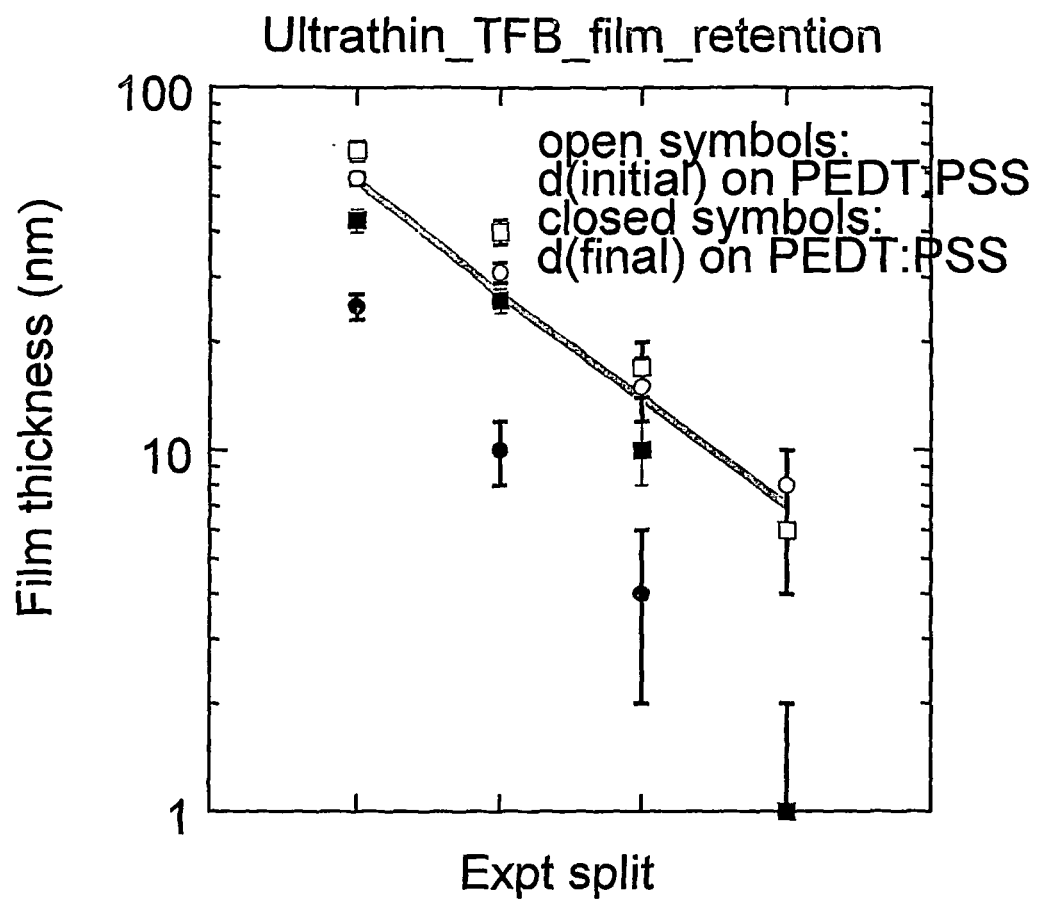
FIG. 2 shows the relationship between film thickness and film retention.

(6. The preferred hole-injection interlayer thickness is governed by optimizing electron-hole capture in the desired region of the device and can be found by experiments. Typically, for a number of polyfluorene-derived emitters, the optimal thickness lies in the range 5-20 nm, which is readily achieved with the methods disclosed here. The film thickness can be controlled accurately between 5-300 nm. Typical results are shown in FIG. 2. See also Example 3 below.

c. The substrate is then optionally baked for 60 min under nitrogen on a hotplate set at 180° C.

d. The film is then washed with mixed xylenes on a spinner chuck (10-s soak, followed by spin-off at 8000 rpm).

e. Poly(9,9-dioctylfluorene-alt-[benzo-2-thia-1,3-diazole-4,7-diyl]) (F8BT) is then spin-cast from a 1.0 w/v % toluene solution under nitrogen to give a 65-70 nm thick film.

f. The substrate is then baked for 3 min under nitrogen on a hotplate set at 120° C.

g. 3-nm-thick Ca followed by 120-nm-thick Al is evaporated onto the film through a shadow mask at a base pressure of 2-4×10$^{-6}$ mbar.

Figure 3:
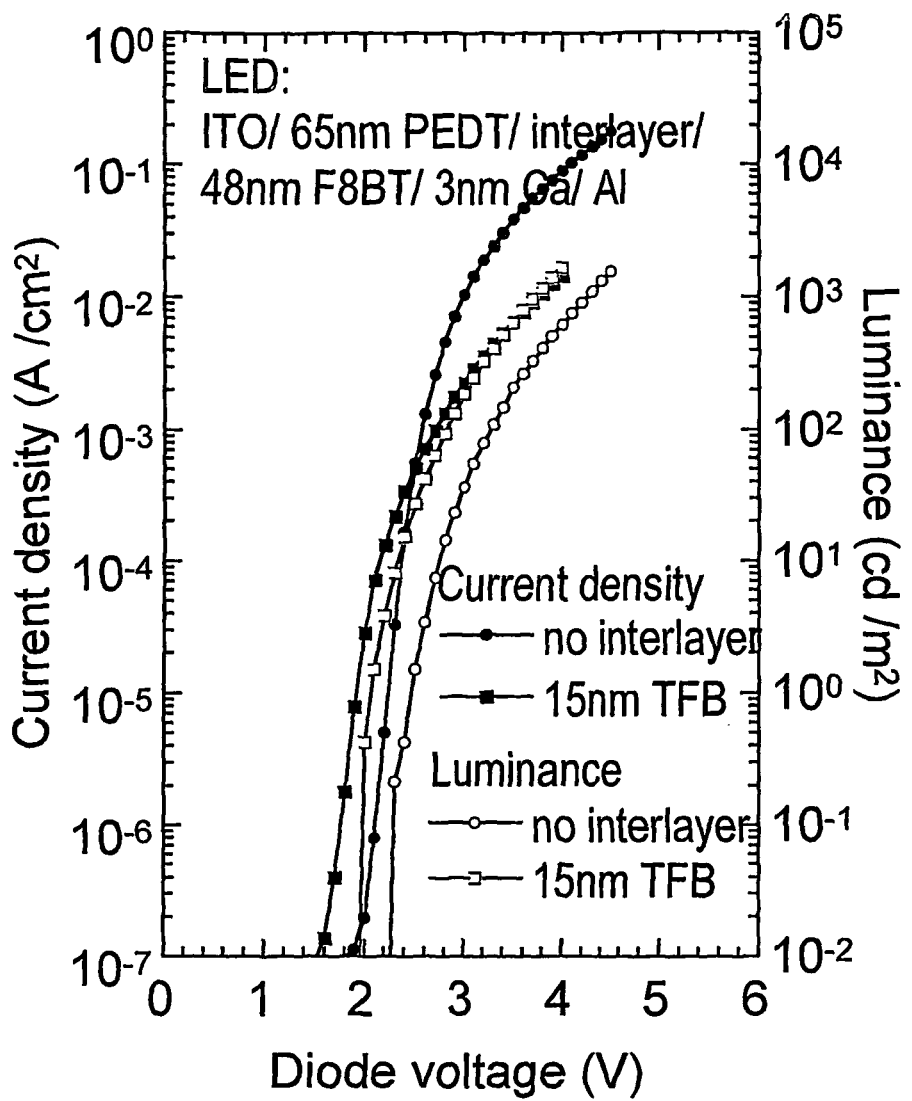
FIG. 3 shows device characteristics of a device with a TFB interlayer.
Figure 4:
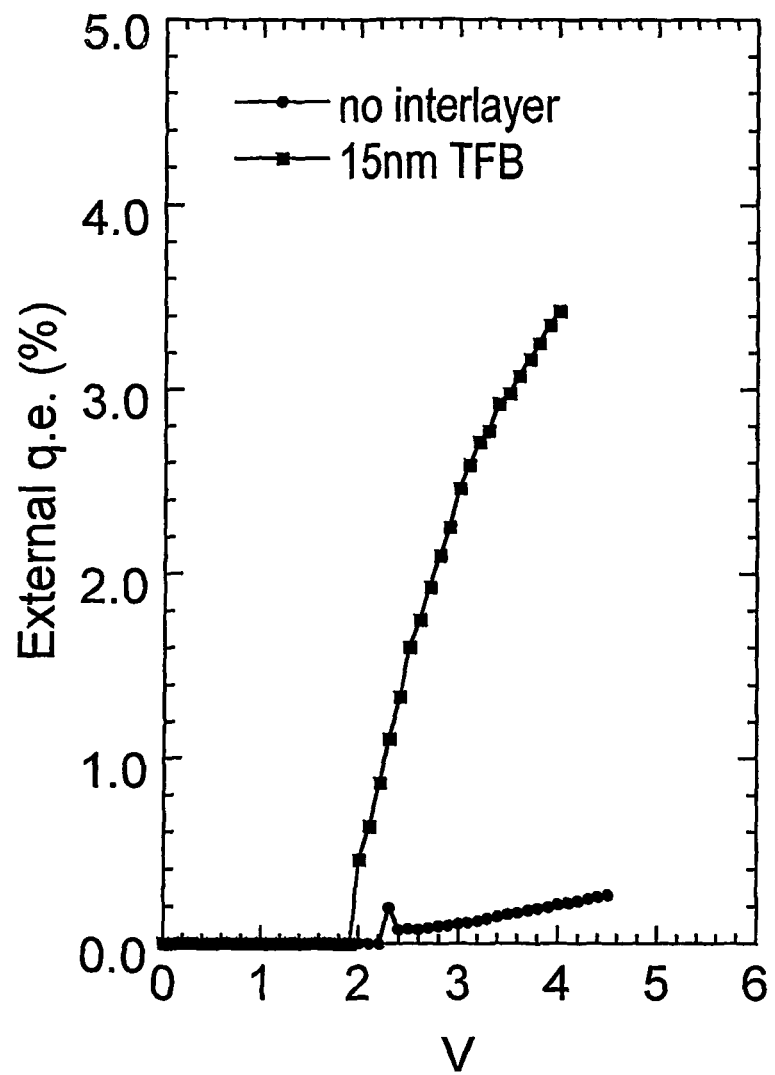
FIG. 4 shows device characteristics for the analogous device to that reported in FIG. 3, without the TFB interlayer.

When the device is driven in forward bias (Ca/Al as cathode and ITO as anode), a large forward-biased diode current with light emission is obtained. Device characteristics are compared in FIGS. 3 and 4 with an analogous device without the TFB interlayer. The quantum efficiency is improved by a factor of 15, and the drive voltage for 1000 cd/m$^2$ for example is reduced from 4.25 to 3.70 V with the TFB interlayer. The improvement in drive voltage is significant because of the strong scaling with device operational lifetime. In this example, the hole-transport interlayer acts not only as hole-transport/electron-blocking but also as a buffer layer to interfacial electrochemistry. As a result the operational lifetime is increased by more than a factor of 10.

Example 2

F8BT-TFB-Blend-Emitter LED

As in Example 1, but the light-emitting polymer layer in step (e) is a 1:1 blend of F8BT and TFB to give a 1.4 w/v % mixed-xylenes solution.

The operational lifetime, quantum efficiency and the voltage for desired brightness is enhanced with the presence of a well-defined hole-transporting-and-electron-blocking interlayer at the anode interface of thickness in the 10-15 nm range. Depending on the blend formulation, an improvement in quantum efficiency by 20-100% without an associated voltage penalty has been found. This indicates that even with a hole-transporting polymer formulated into the blend, fabrication of a well-defined and continuous hole-transporting layer of thickness 5-20 nm at the anode contact can further improve performance and stability.

Example 3

F8BT-Emitter LED

Figure 5:
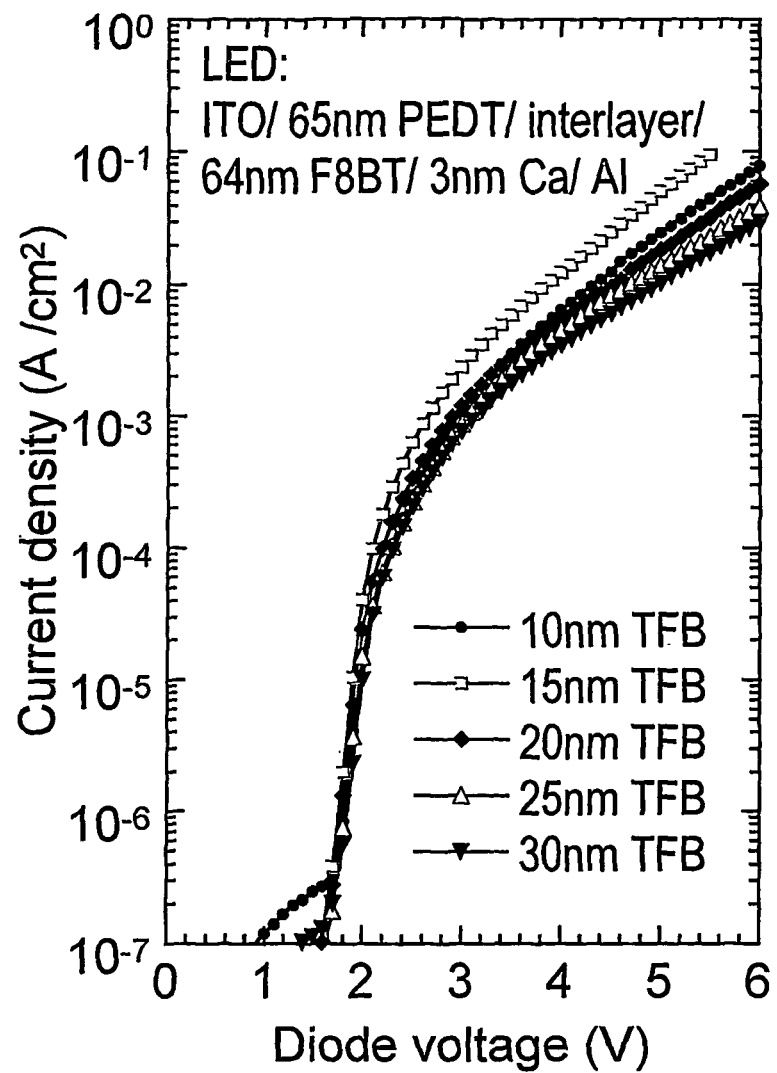
FIG. 5 shows the current density vs diode voltage as measured in Example 3.
Figure 6:
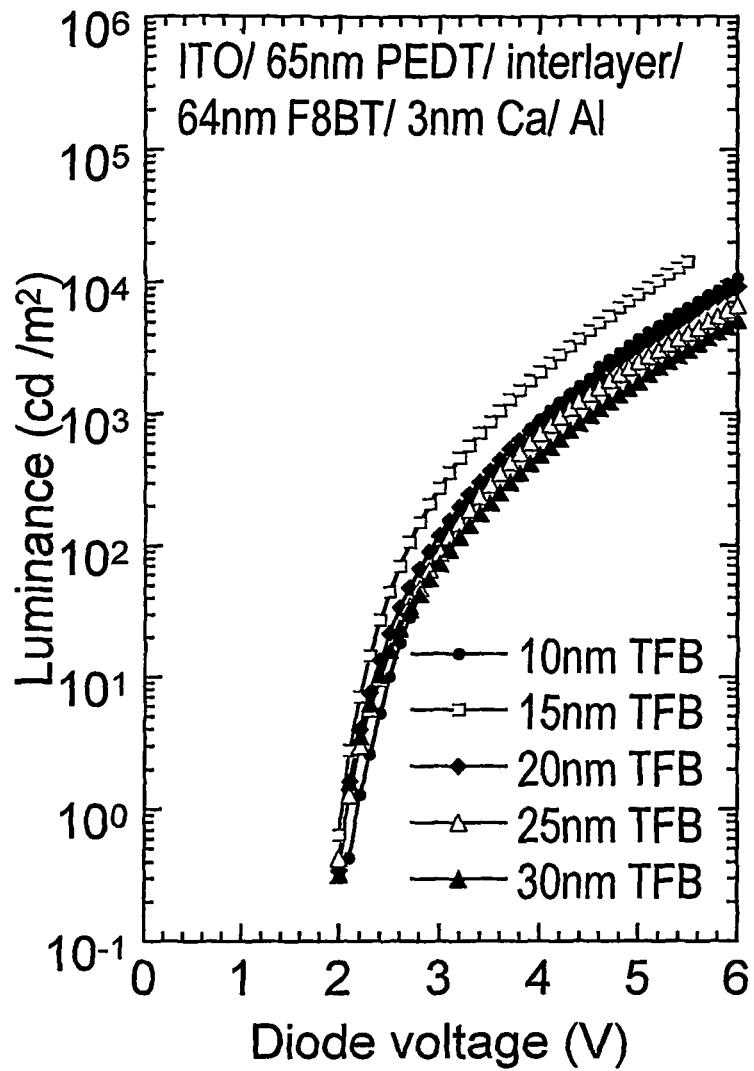
FIG. 6 shows the luminescence vs diode voltage as measured in Example 3.
Figure 7:
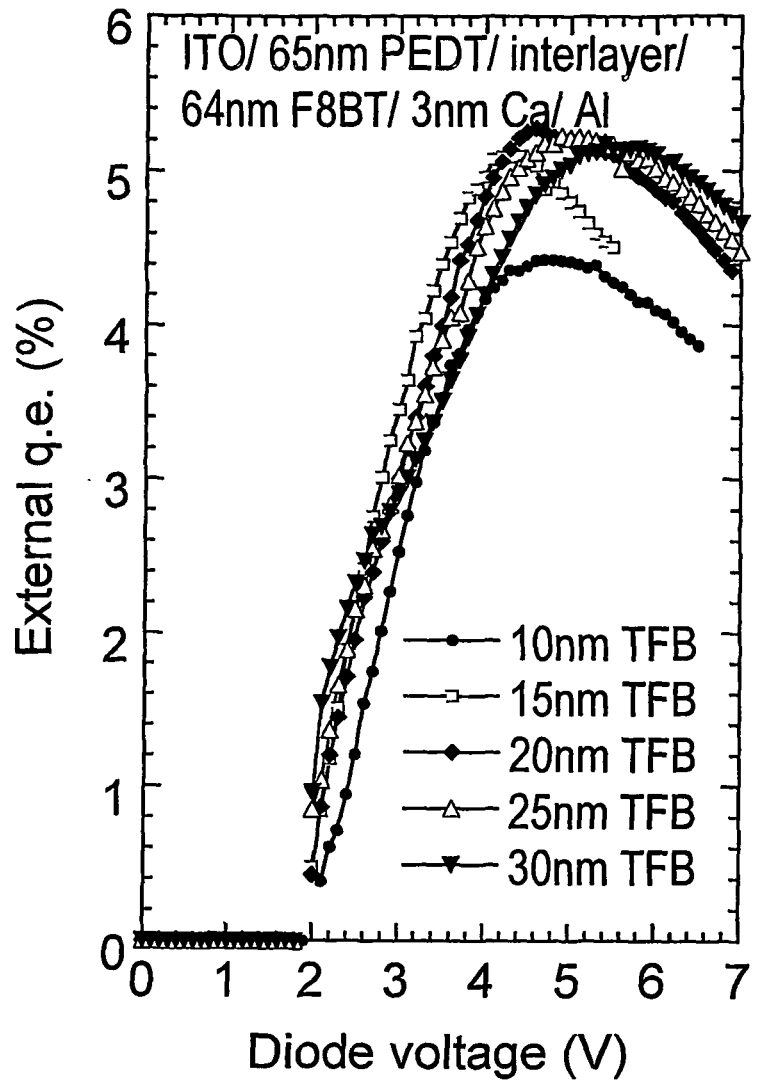
FIG. 7 shows the external quantum efficiency vs diode voltage as measured in Example 3.

Same as Example 1, but the thickness of the TFB interlayer in step (b) is controlled with 5-nm resolution between 10 nm and 30 nm. The thickness of the interlayers is confirmed by atomic force profilometry. The current density, luminance and external quantum efficiency of the devices are shown in FIGS. 5, 6, and 7 respectively. This example is provided to show the benefits of fine control of the interlayer thickness. As a result systematic optimisation of device performance becomes possible.

Example 4

Stacked Hole-Injection Interlayer

As in example 1, but an additional layer of a second hole-transporting polymer is used as the second layer in the interlayer stack. Here this polymer is chosen to be poly(vinylcarbazole) (PVK) formulated with 1.6% I by weight of PVK. The mixture is spin-cast from a 0.25 w/v % chloroform solution under nitrogen to give a 10-nm thick film. The film is then exposed under nitrogen through a photomask to 254-nm deep ultraviolet radiation for 2 min at an illuminance of 1 mW/cm$^2$ on the film surface.

(7. The preferred nature of this second interlayer polymer at the anode interface (if used) is to offer a hole-transport level intermediate between that of the first interlayer polymer and of the light-emitting polymer, while not providing any accessible electron transport level for the leakage of electrons. In this way, a ladder of hole-transport energy levels is arranged to facilitate the hole-injection into the light-emitting polymer itself.

(8. Alternatively this polymer is used as a capping layer to suppress undesirable electrochemical reactions with the light-emitting-polymer that alter the electrical properties of the interface with operation.

PVK partially meets these considerations and is therefore not ideal. Nevertheless an improvement in the low-voltage efficiency is obtained on account of PVK being a better electron blocker than TFB. Therefore this example confirms that such stacked interlayers can be built advantageously with the appropriate polymers.

(B) Crosslinking and Photopatterning of the LEP Layer in LEDs

Example 5

Photopatterned OC1C10-PPV LED a. Photoresist is removed from prepatterned ITO glass substrate using acetone, isopropanol and nitrogen blow-off. The ITO surface is then exposed to an oxygen plasma for 10 min in a barrel etcher (Tegal Barrel Etcher 421; typical conditions: pressure, 450 mbar; power 150 W). Poly(3,4-ethylenedioxythiophene): polystyrenesulfonate (PEDT:PSS) formulated with a PEDT-to-PSS ratio of 1:15 is then spin-cast from an aqueous solution to give a 60-70-nm thick film. The film is baked for 15 min under nitrogen on a hotplate set at 150° C.
b. Poly(2-methoxy-5-(3,5-dimethyl)octyl-1,4-phenylenevinylene) (OC10-PPV) formulated with 2% ethylene glycol bis(4-azido-2,3,5,6-tetrafluorobenzoate) (I) by weight of OC1C10 is then spin-cast from a 0.5 w/v % mixed-xylenes solution under nitrogen to give a 47-nm thick film. The film is then exposed under nitrogen through a photomask to 254-nm deep ultraviolet radiation for 2 min at an illuminance of 1 mW/cm$^2$ on the film surface, and then developed with toluene.
c. The substrate is then optionally baked for 5 min under nitrogen on a hotplate set at 200° C.
d. 3-nm-thick Ca followed by 120-nm-thick Al is evaporated onto the film through a shadow mask at a base pressure of 2-4×10$^{-6}$ mbar.

Figure 8:
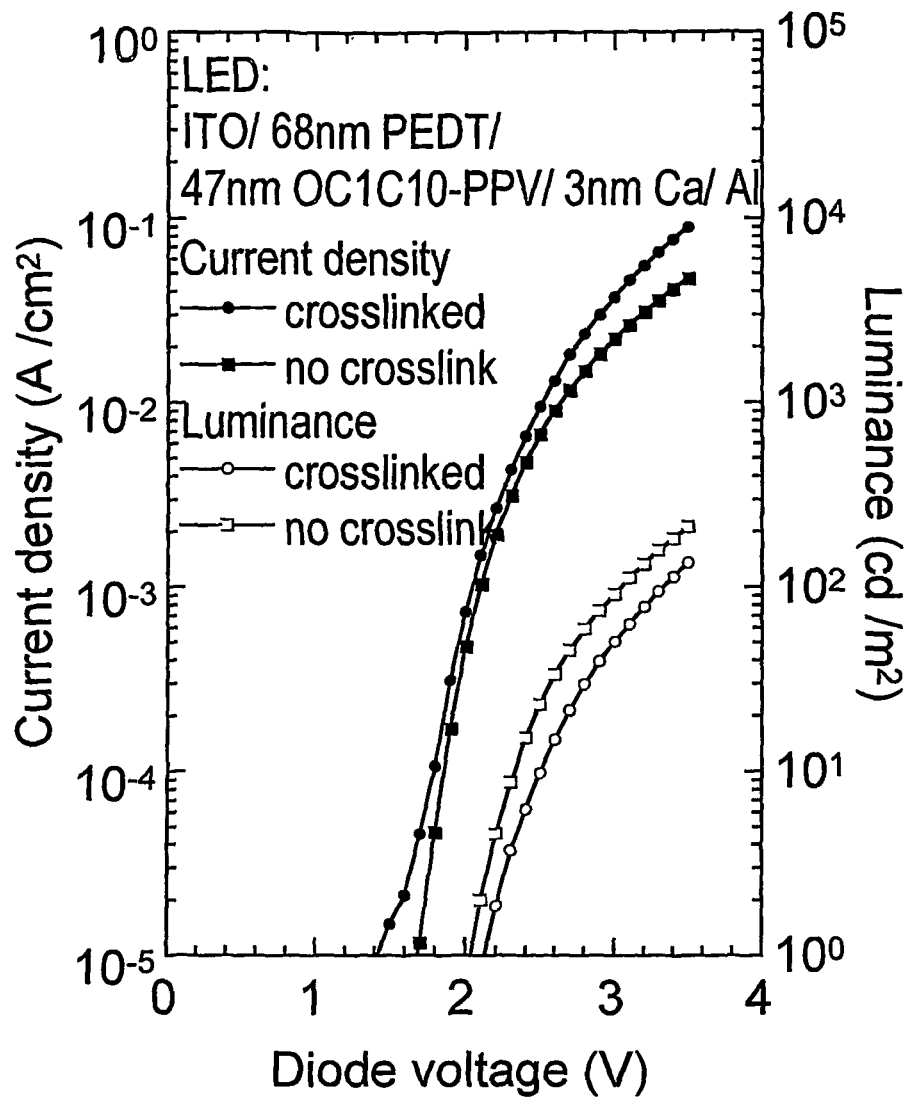
FIG. 8 shows a comparison of device characteristics of the device according to Example 5 and an analogous device without the crosslinker.

When the device is driven in forward bias (Ca/Al as cathode and ITO as anode), a large forward-biased diode current with light emission is obtained. Device characteristics are compared in FIG. 8 with an analogous device without the crosslinker and photopatterning. Similar current densities are obtained in both cases. Therefore the ability to drive a current through the device is not degraded. Quantum efficiency is poorer for the photopatterned device, but this can be raised back to pristine levels by reducing the crosslinker fraction to <0.5% by weight. This example is provided to show that the crosslinking process described here can be applied to the LEP layer. The requisite bipolar injection and electroluminescence from the LEP is not strongly degraded even at a relatively high crosslinker ratio and a small film thickness which makes current-voltage chararacteristics particularly sensitive to the injection contacts. These devices are therefore not optimised: the OC1C10-PPV thickness of 47 nm is considerably smaller than the optimum of 60-65 nm, and the crosslinker fraction used is in considerable excess of what is needed (ca. 0.5%).

(B) Crosslinking and Photopatterning of the Channel Layer in FETs

Example 6

Crosslinked/Photopatterned P3HT-Channel Bottom-Gate FET a. Prepatterned p+-doped Si substrates with a 200-nm silicon oxide top dielectric layer and gold source-drain contact pads are cleaned by exposing to an oxygen plasma for 10 min in a barrel etcher (Tegal Barrel Etcher 421; typical conditions: pressure, 450 mbar; power 200 W), and then rinsed with CMOS-grade water, iso-propanol and then dried off in a nitrogen jet. Prepatterned channel length is 10 μm and channel width is 2 mm. Hexamethyldisilazane is spin onto the substrate at 900 rpm, 30 s, and then the substrate is baked in air on a hotplate for 2 min at 120° C.
b. Regio-regular poly(3-hexylthiophene) (P3HT) formulated with 5% ethylene glycol bis(4-azido-2,3,5,6-tetrafluorobenzoate) (I) by weight of P3HT is then spin-cast from a 1.8 w/v % chloroform solution to give a 50-nm thick film. The film is then exposed under nitrogen through a photomask to 254-nm deep ultraviolet radiation for 2 min at an illuminance of 1 mW/cm$^2$ on the film surface, and then developed with chloroform, followed by nitrogen blow-off
c. The device is then annealed under nitrogen on hotplate at 100° C. for 2 min.

Figure 9:
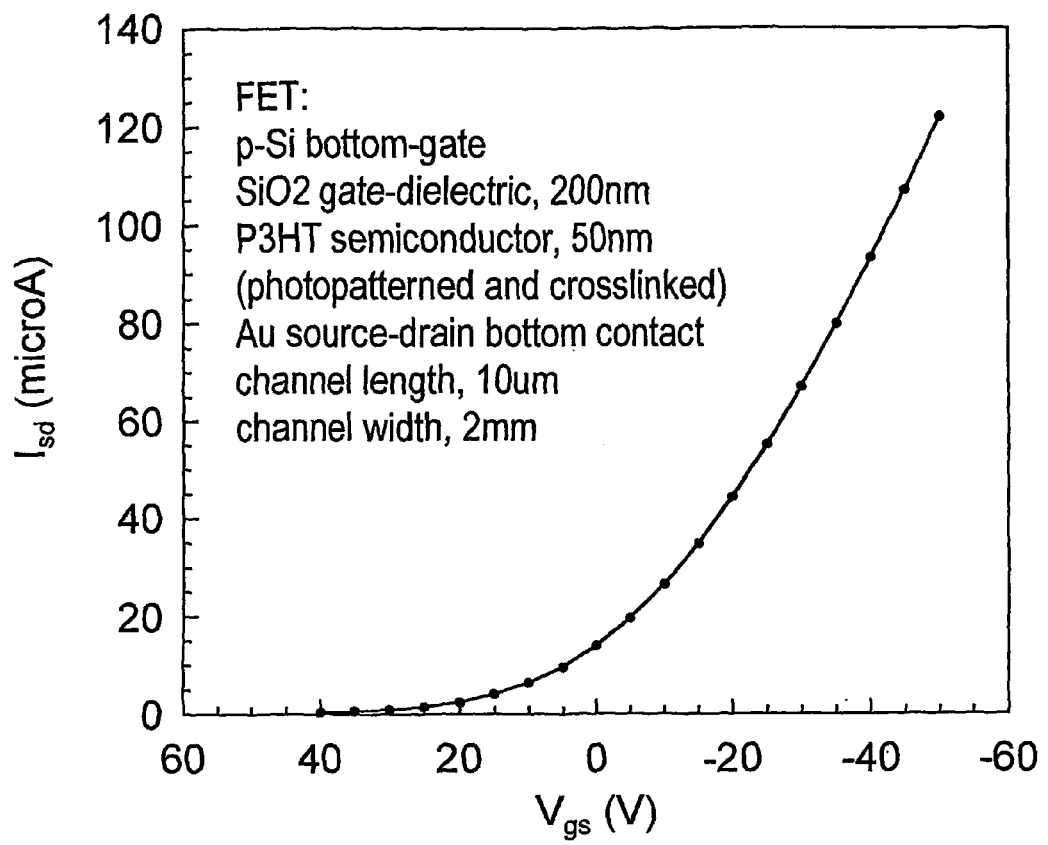
FIG. 9 shows the transfer characteristics of the FET according to Example 6.

The transfer characteristic of this FET is shown in FIG. 9. The threshold gate voltage ($V_{th}$) is ca. −0 V. A strong turn-on of the channel conductivity is found when the gate voltage ($V_g$) is increased above this threshold. An "on" source-drain channel current of 100 μA is obtained for a drain voltage ($V_{ds}$) of −30 V, and gate voltage ($V_{gs}$) of −50 V. On-off ratio is better than 100 for gate voltage −50 V to +50 V. The FET mobility extracted by traditional equations from the $I_{sd}$–$V_{gs}$ slope in the linear regime is near 3×10$^{-2}$ cm$^2$/V s. Typical mobility for pristine P3HT films spin-cast without the crosslinker and photoexposure is 10$^{-1}$-10$^{-2}$ cm$^2$/Vs. Forward and reverse scan characteristics are superimposable. This example is provided to prove that the desirable field-effect mobility can be substantially retained after the photocrosslinking process described here even at such a relatively high crosslinker fraction. Field-effect mobility is particularly sensitive to the presence of defects and impurities that tend to segregate to the interfaces. This finding validates the approach as a viable means of patterning polymer transistors with high field-effect mobilities. In practical devices, the FET transistor will be constructed on other substrates, such as glass, polyethylene, poly(ethyleneterepthalate), or other polymeric materials, and with other materials as the source, drain and gate contacts, such as conducting polymer-based materials. Also the molecular weight of the field-effect polymer used will be larger than the one used here (ca. 30,000) by an order of magnitude or so. Therefore the crosslinker fraction used can be further reduced to below 1%, further enhancing the attractive features of this process.

Example 7

Crosslinked/Photopatterned TFB-Channel Top-Gate FET

As in Example 6, but the field-effect polymer is replaced with TFB used at a concentration of 1.8 w/v % in mesitylene blended with 1.3% ethylene glycol bis(4-azido-2,3,5,6-tetrafluorobenzoate) (I) by weight of TFB. This is spun onto the substrate at 1600 rpm, 60 s, to give a 30 nm film. The substrate has prepatterned 20-nm gold source and drain contacts with channel length of 5 μm and channel width of 10 mm (interdigited array). The substrate is then exposed in nitrogen through a photomask to 254-nm radiation for 2 min to crosslink the TFB film, and developed by 10-s mesitylene soak followed by spin-off at 6000 rpm, 30 s.

Bis(dimethylvinylbenzocyclobutene) disiloxane monomer in mesitylene (Cyclotene® from Dow Chemical Company, MI, U.S.A.) is diluted to a concentration of 12.7 weight/vol % is spin onto the TFB film at 6000 rpm, 60 s, to give a 200 nm film. Note, if the TFB film is not crosslinked, application of this BCB-based monomer/mesitylene solution will immediately redissolve the formed TFB layer. The substrate is then baked under nitrogen on a hotplate for 10 s at 290° C.

PEDT:PSS (available from HC Starck of Leverkusen, Germany as "Baytron P"®) is applied to give the top-gate electrode as described in Example 1.

Figure 10:
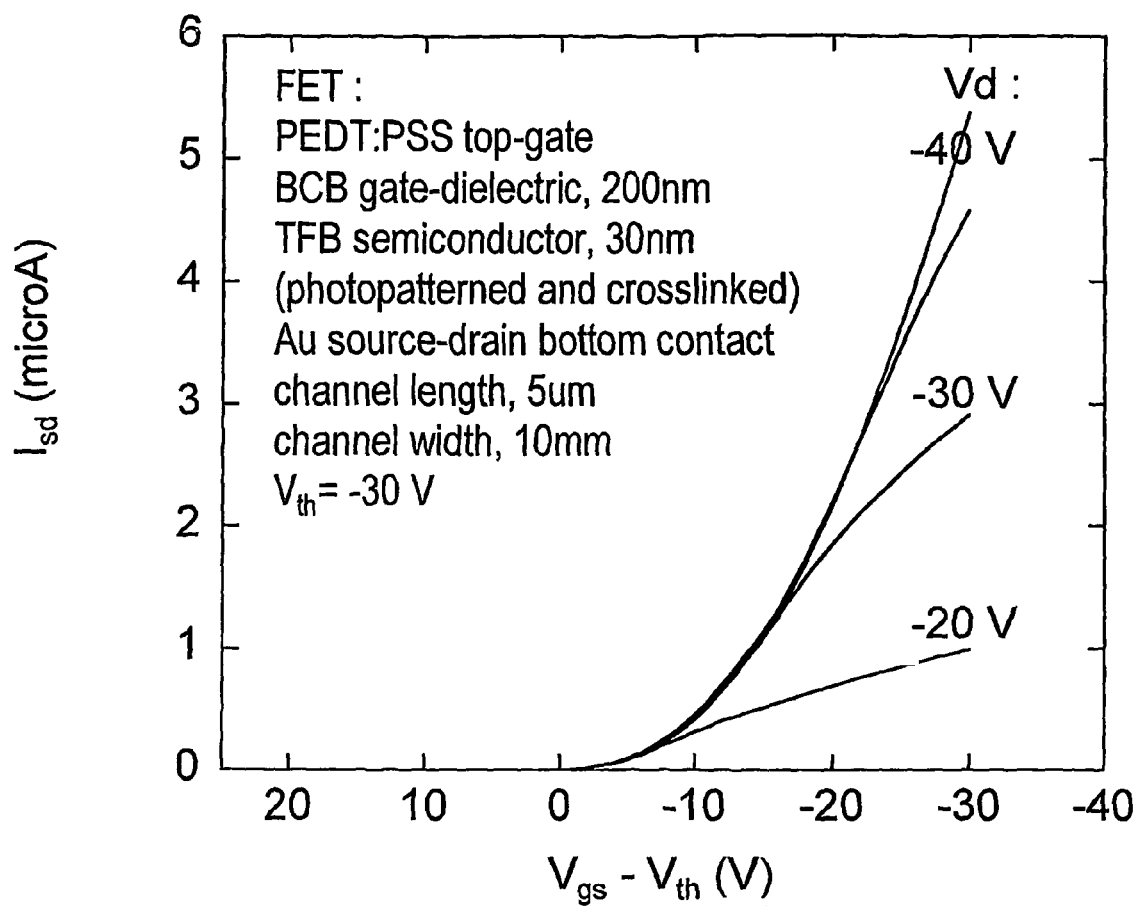
FIG. 10 shows the transfer characteristics of the device according to Example 7.
Figure 11:
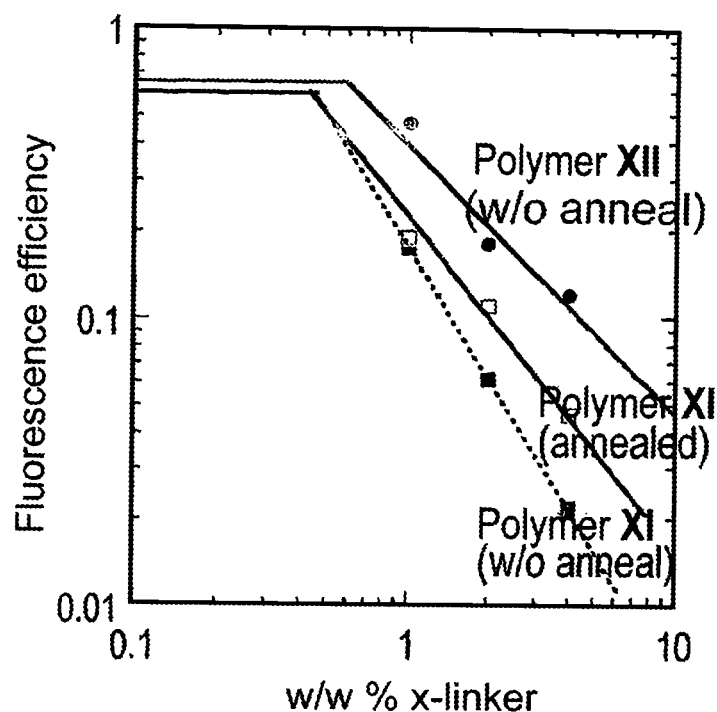
FIG. 11 shows the photoluminescence efficiency for the crosslinking moiety ethylene diol bis(p-azido-2,3,5,6-tetrafluorobenzoate) in the two different polymers. Exposure conditions were: 254-nm Hg line; 1 mW/cm$^2$, 2 min.
Figure 11:
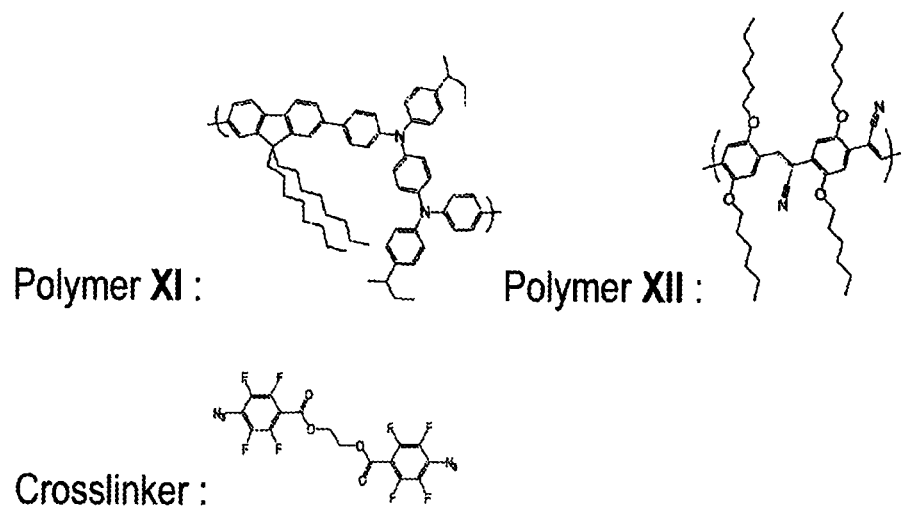

The transfer characteristics of this device are given in FIG. 10. The threshold gate voltage ($V_{th}$) is ca. −30 V. This is largely limited by traces of ionic impurities in the TFB field-effect polymer. A strong turn-on of the channel conductivity is found when the gate voltage ($V_{gs}$) is increased above this threshold. An "on" source-drain channel current ($I_{sd}$) of few microAmperes is obtained for a drain voltage ($V_{ds}$) of −20 V, and ($V_g-V_{th}$) of −30 V. On-off ratio is better than 1000. The FET mobility extracted by traditional equations from the $I_{sd}-V_{gs}$ slope in the linear regime is near $4 \times 10^{-4}$ cm$^2$/Vs. This example is provided to show that the photocrosslinked field-effect polymer can be advantageously combined with a broad range of subsequent solvent processing steps (for example, to deposit the gate dielectric, interlevel planarisation layers, interconnects etc) that would otherwise destroy the integrity of the first-formed polymer film. The field-effect mobility of pristine spin-cast TFB films is $10^{-3}$-$10^{-4}$ cm$^2$/Vs. The mobility therefore is not degraded, as in Example 6, proving that the methods and processes described here is compatible with a range of semiconducting polymers of widely differing properties.

Example 8

Donor-Acceptor Multilayered Photoconductive Device

Figure 12:
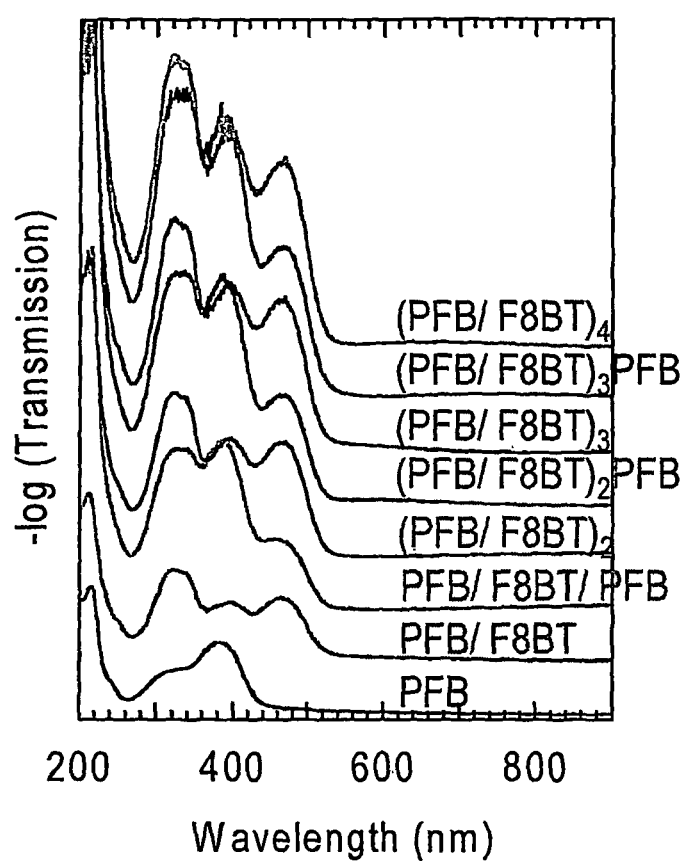
FIG. 12 shows the UV-vis absorption spectrum collected during the multilayer fabrication described in Example 8.

Multiple alternating layers of a hole-transporting donor polymer ("PFB") and an electron-transporting acceptor polymer ("F8BT") are prepared on a glass substrate patterned with a lateral interdigitated array. The donor-acceptor terminology has been incorporated here to indicate that photoexcitations are dissociated at the interface between these two polymers to leave a hole on the PFB-side of the interface and an electron on the F8BT-side of the interface. Each of the layers is approximately 40 nm thick. A UV-vis absorption spectrum collected at each stage of the multilayer fabrication is shown in FIG. 12. The quality of the film is excellent as judged by the absence of optical scattering in the transparent window and the regular evolution of the interference fringe pattern as the overall film thickness approaches the optical length scale. In fact the spectrum builds up in a systematic way with each addition of a film of PFB or F8BT to the multilayer stack. This means that a large number of subsequent polymer layers can be deposited with controlled thickness and without impairing the integrity of the underlying layers. This is otherwise impossible to achieve without the crosslinking moiety technology described in this invention.

Figure 13:
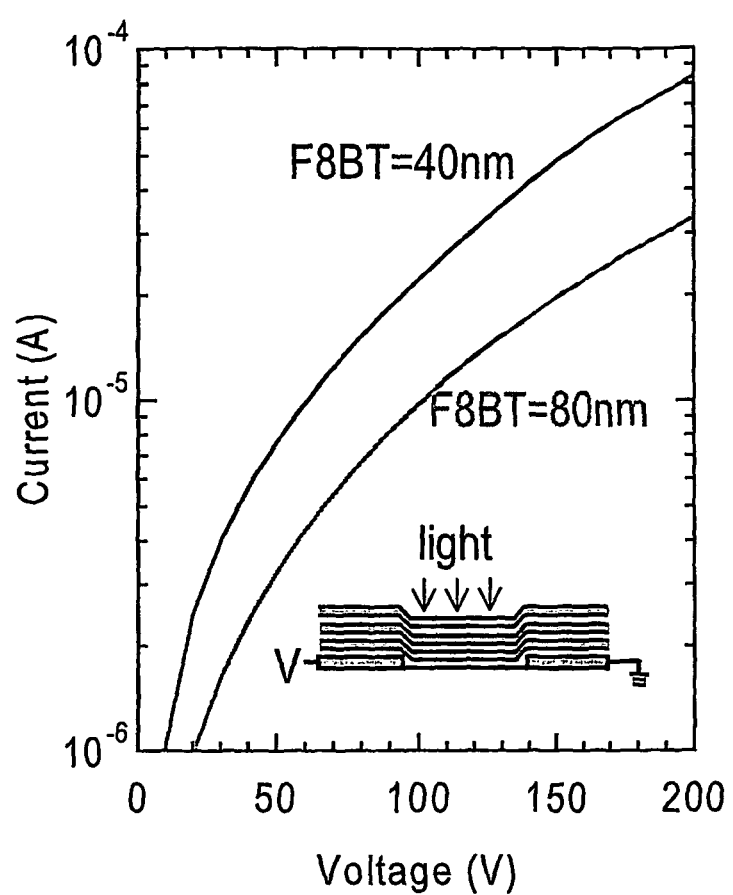
FIG. 13 shows photocurrent plots for the device described in Example 8.

Because the exciton diffusion length is limited in organic materials, it is advantageous to have the individual donor and acceptor film thicknesses smaller than the exciton diffusion length (typically 20 nm) so that maximum charge carrier concentration can be obtained to provide a large photoconductive response. To test this possibility, two multilayer stacks were fabricated in which the F8BT thickness was 40 nm in one stack but 80 nm in the second stack (device structure shown in the inset in FIG. 13). The PFB layer thickness was kept identical in both stacks (ca. 40 nm). The stack was illuminated with 457-nm (Ar-ion laser) at which only the F8BT component absorbs. The cumulated F8BT thickness in the stack was such that practically all the light traversing the stack was absorbed. The resultant photocurrent plots are shown in FIG. 13, demonstrating a factor of two increase in the photoconductivity of the donor-acceptor stack with the thinner F8BT layers, consistent with expectations.

This example is provided to further show the utility of the approach in opening up the possibility to fabricate multilayered organic electronics to take advantage of complementary donor-acceptor, and electron-hole transporting properties.

The invention claimed is:

1. A method of forming a polymer device including the steps of:
   (i) depositing on a substrate a solution comprising a semiconductive polymer or oligomer and a crosslinking moiety, to form a layer; and,
   (ii) curing the layer formed in step (i) under conditions to form an insoluble crosslinked polymer;
   wherein the crosslinking moiety is present in step (i) in an amount in the range of from 0.05 mol % to less than 5 mol % based on the total number of moles of repeat units of the polymer or oligomer and the crosslinking moiety in the solution.

2. A method according to claim 1, wherein the method comprises a further step of depositing a solution containing a second polymer on the crosslinked polymer formed in step (ii).

3. A method according to claim 1, wherein the method comprises a further step of chemically modifying the insoluble crosslinked polymer.

4. A method according to claim 1, comprising patterning the polymer formed in step (ii) by curing only a part of the layer formed in step (i) and removing uncured parts.

5. A method according to claim 4, comprising removing uncured parts by washing with a solvent.

6. A method according to claim 1, wherein the crosslinking moiety is sensitive to ultraviolet radiation having a wavelength in the range 200 nm to 400 nm and the conditions in step (ii) comprise exposing the layer to UV radiation having a wavelength in the range 200 nm to 400 nm in an inert atmosphere.

7. A method according to claim 1, wherein the crosslinked polymer formed in step (ii) is partially, substantially or fully conjugated.

8. A method according to claim 1, wherein the crosslinked polymer comprises at least one member of the group consisting of fluorene, an indenofluorene, a triarylamine, a thiophene, phenylene, phenylenevinylene, and substituted azole repeat units.

9. A method according to claim 1, wherein the thickness of the layer deposited in step (i) is in the range of from 1 nm to 500 nm.

10. A method according to claim 1, wherein the polymer device is a device selected from the group consisting of a polymer LED device, a polymer waveguide LED device, a polymer distributed Bragg reflector, a polymer microcavity LED device, a polymer FET device, a polymer photodetector, and a polymer photovoltaic device.

11. A method according to claim 1, wherein the crosslinking moiety is part of the main chain of the polymer or oligomer or is attached as a side chain to the polymer or oligomer.

12. A method according to claim 11, wherein the polymer or oligomer comprises a structural unit comprising the crosslinking moiety and having a general formula III or IV:

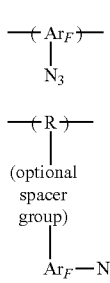

where $Ar_F$ comprises a substituted or unsubstituted fluorinated aryl group and R is a structural unit in the main chain of the polymer or oligomer.

13. A method according to claim 1, wherein the crosslinking moiety is mixed with the polymer or oligomer in the solution.

14. A method according to claim 13, wherein the crosslinking moiety has a general formula I:

where $Ar_F$ comprises a substituted or unsubstituted fluorinated aryl group.

15. A method according to claim 14, wherein the crosslinking moiety has a general formula II;

where $Ar_F$ and $Ar_F$ independently each comprise fluorinated aryl and L comprises an optional divalent or multivalent linker group.

16. A method according to claim 13, wherein the polymer or oligomer is present in an amount of from 0.5 wt % to 2.5 wt % in the solution prior to addition of the crosslinking moiety.

17. A polymer device obtainable by the method as defined in claim 1.

18. A polymer device according to claim 17, wherein the polymer device is a waveguide LED device comprising a core layer and at least one cladding layer, wherein the core layer and the at least one cladding layer each comprise a crosslinked polymer.

19. A solution containing a semiconductive polymer or oligomer and a crosslinking moiety, wherein the crosslinking moiety is present in an amount of from 0.05 mol % to less than 5 mol % based on the total number of moles of repeat units of the polymer and the crosslinking moiety in the solution.

20. A solution according to claim 19, wherein the crosslinking moiety is mixed with the polymer in the solution.

21. A solution according to claim 20, wherein the crosslinking moiety has general formula II:

where $Ar_F$ and $Ar_F$ each is a fluorinated aryl group and L comprises an optional divalent or multivalent linker group.

22. A method of forming a polymer device comprising the steps of:
(i) depositing on a substrate a solution comprising a semiconductive polymer or oligomer and a crosslinking moiety to form a layer;
(ii) curing the layer formed in step (i) under conditions to form an insoluble crosslinked polymer; and
(iii) annealing the insoluble polymer formed in step (ii), wherein the crosslinking moiety is present in step (i) in an amount in the range of from 0.05 mol % to less than 5 mol % based on the total number of moles of repeat units of the polymer or oligomer and the crosslinking moiety in the solution.

23. A method according to claim 1, wherein the crosslinking moiety is present in step (i) in an amount in the range of from 0.05 mol % to 3 mol % based on the total number of moles of repeat units of the polymer or oligomer and the crosslinking moiety in the solution.

24. A method according to claim 22, wherein the crosslinking moiety is present in step (i) in an amount in the range of from 0.05 mol % to 3 mol % based on the total number of moles of repeat units of the polymer or oligomer and the crosslinking moiety in the solution.

* * * * *